United States Patent
Williams et al.

(10) Patent No.: US 11,016,574 B2
(45) Date of Patent: May 25, 2021

(54) MILLIMETER-WAVE-RADAR-BASED ELECTROMAGNETIC APPARATUS

(71) Applicant: Rogers Corporation, Chandler, AZ (US)

(72) Inventors: Shawn P. Williams, Andover, MA (US); Gianni Taraschi, Arlington, MA (US); Sara G. Canzano, Boston, MA (US); Kristi Pance, Auburndale, MA (US); Christopher Brown, Natick, MA (US); Karl E. Sprentall, Medford, MA (US); Roshin Rose George, Burlington, MA (US)

(73) Assignee: ROGERS CORPORATION, Chandler, AZ (US)

( * ) Notice: Subject to any disclaimer, the term of this patent is extended or adjusted under 35 U.S.C. 154(b) by 0 days.

(21) Appl. No.: 16/663,443

(22) Filed: Oct. 25, 2019

(65) Prior Publication Data
US 2020/0133398 A1 Apr. 30, 2020

Related U.S. Application Data

(60) Provisional application No. 62/753,337, filed on Oct. 31, 2018.

(51) Int. Cl.
*G06F 3/048* (2013.01)
*G06F 3/01* (2006.01)
(Continued)

(52) U.S. Cl.
CPC .............. *G06F 3/017* (2013.01); *A61B 5/681* (2013.01); *G06F 1/163* (2013.01); *G06F 3/011* (2013.01);
(Continued)

(58) Field of Classification Search
CPC .......... G06F 3/017; G06F 1/163; G06F 3/011; G06F 1/1698; G06K 9/00335;
(Continued)

(56) References Cited

U.S. PATENT DOCUMENTS 6,008,755 A 12/1999 Ishikawa et al.
6,188,360 B1 2/2001 Kato et al.
(Continued)

FOREIGN PATENT DOCUMENTS

EP 2953007 A1 12/2015

OTHER PUBLICATIONS

International Search Report and Written Opinion for International Application No. PCT/US2019/058515 dated ISR/WO, dated Jan. 22, 2020; 18 pgs. technically related to U.S. Appl. No. 16/663,441.
(Continued)

*Primary Examiner* — Pei Yong Weng
(74) *Attorney, Agent, or Firm* — Cantor Colburn LLP

(57) ABSTRACT

A wearable electromagnetic, EM, apparatus includes: at least one antenna operable in a millimeter-wave-radar-based, MWRB, application; at least one computer processor disposed in signal communication with the at least one antenna; an attachment system configured and adapted to attach to an actor; the at least one antenna and the at least one computer processor disposed in a supported relationship with the attachment system, such that the attachment system with the supported at least one antenna and the at least one computer processor at least partially forms a wearable apparatus that is wearable by the actor.

41 Claims, 12 Drawing Sheets

(51) Int. Cl.
*G06K 9/00* (2006.01)
*H01Q 9/04* (2006.01)
*A61B 5/00* (2006.01)
*G06F 1/16* (2006.01)
*H01Q 1/27* (2006.01)

(52) U.S. Cl.
CPC ......... *G06K 9/00335* (2013.01); *H01Q 1/273* (2013.01); *H01Q 9/0485* (2013.01)

(58) Field of Classification Search
CPC ...... H01Q 9/0485; H01Q 1/273; A61B 5/681; G01S 13/06; G01S 13/88
See application file for complete search history.

(56) References Cited

U.S. PATENT DOCUMENTS

| | | | | |
|---|---|---|---|---|
| 6,198,450 | B1* | 3/2001 | Adachi | H01Q 9/0485 |
| | | | | 343/753 |
| 6,356,246 | B1 | 3/2002 | Nakamura et al. | |
| 9,935,065 | B1* | 4/2018 | Baheti | H01L 23/49822 |
| 2006/0092079 | A1* | 5/2006 | de Rochemont | H01Q 15/006 |
| | | | | 343/700 MS |
| 2015/0049487 | A1* | 2/2015 | Connor | F21V 33/0008 |
| | | | | 362/277 |
| 2016/0178730 | A1* | 6/2016 | Trotta | G01S 7/354 |
| | | | | 342/175 |
| 2017/0125909 | A1 | 5/2017 | Pance et al. | |
| 2018/0074173 | A1* | 3/2018 | Trotta | H01Q 21/293 |
| 2018/0196501 | A1* | 7/2018 | Trotta | B60R 25/245 |
| 2019/0108375 | A1* | 4/2019 | Ganesan | G06K 7/10396 |
| 2019/0113609 | A1* | 4/2019 | Baheti | H01Q 1/2283 |
| 2020/0026360 | A1* | 1/2020 | Baheti | G06F 3/0416 |
| 2020/0026361 | A1* | 1/2020 | Baheti | G06F 3/017 |

OTHER PUBLICATIONS

Lien, J. et al., "ACM Reference Format Soli: Ubiquitous Gesture Sensing with Millimeter Wave Radar", ACM Trans. Graph. Article, Jul. 1, 2016 (Jul. 1, 2016), XP055647692, Retrieved from the Internet: URL:http://www.ivanpoupyrev.com/wp-content/uploads/2017/01/siggraph_final.pdf [retrieved on Nov. 29, 2019].

Malhat, H., et al., "Radiation Characteristics Enhancement of Dielectric Resonator Antenna Using Solid/Discrete Dielectric Lenses", Advanced electromagnetics, Feb. 19, 2015 (Feb. 19, 2015), p. 1, XP055728939.

Second Written Opinion for International Application No. PCT/US2019/058515, dated Oct. 14, 2020; 11 pgs. technically related to U.S. Appl. No. 16/663,443.

* cited by examiner

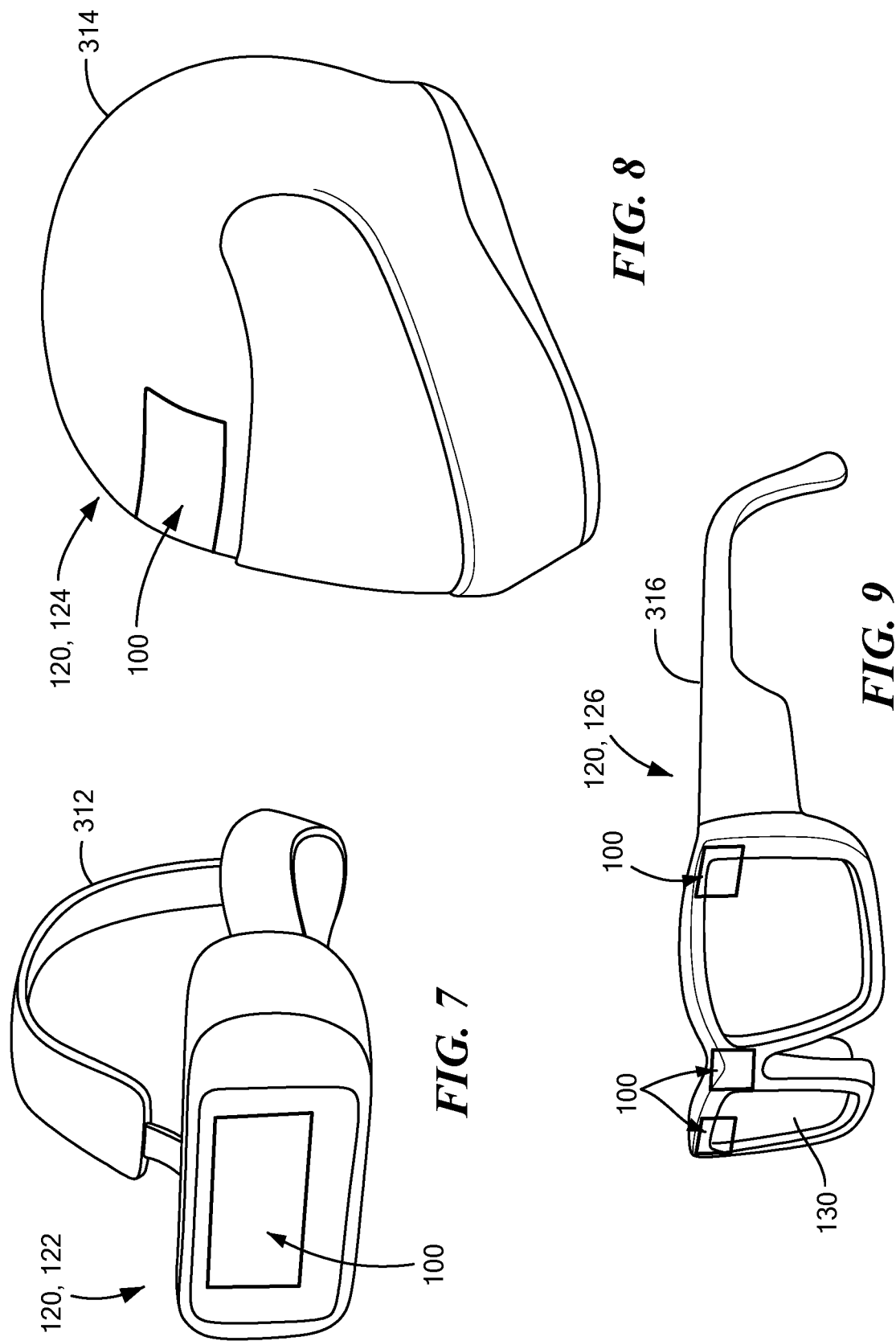

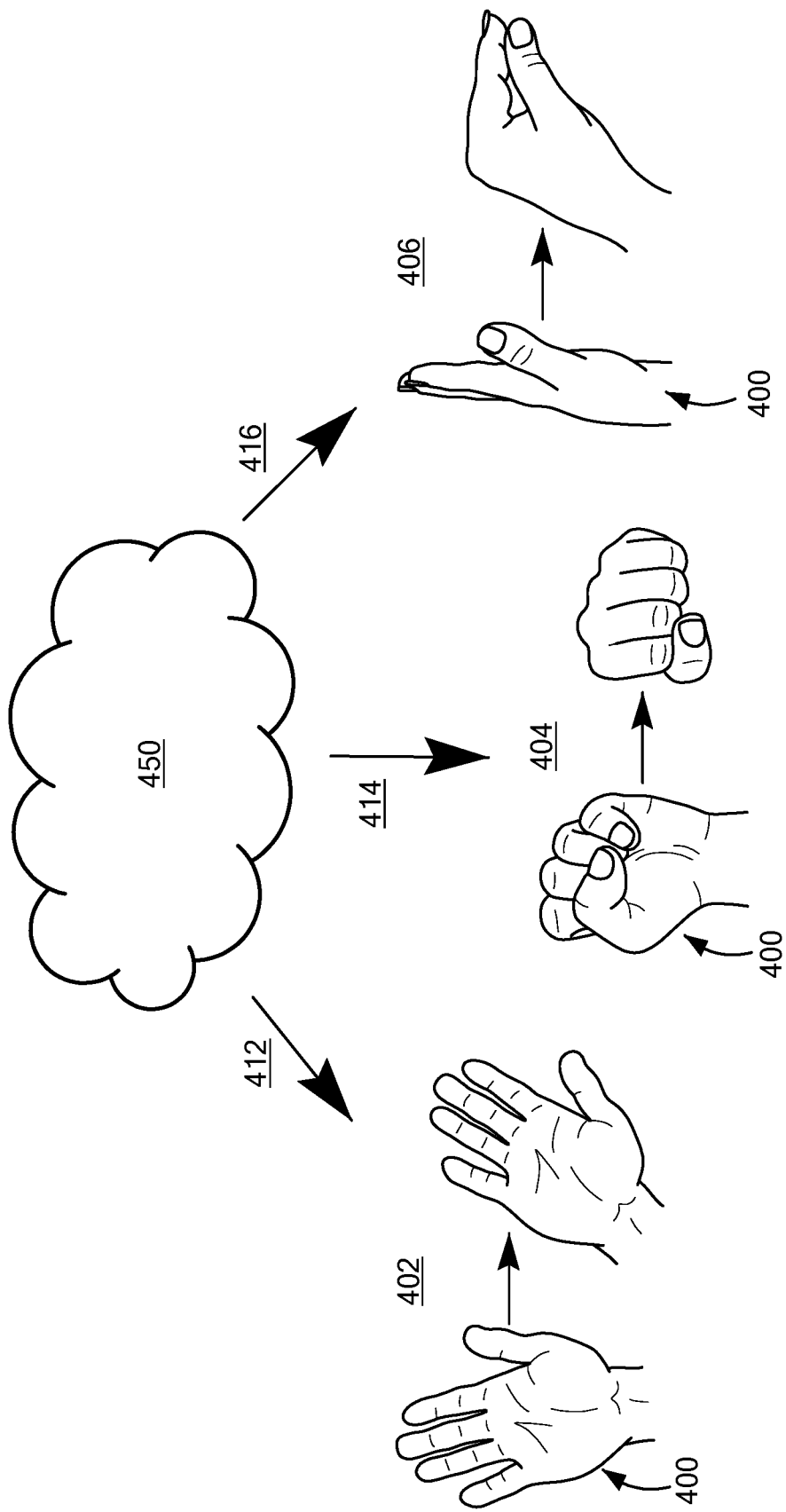

MILLIMETER-WAVE-RADAR-BASED ELECTROMAGNETIC APPARATUS

CROSS REFERENCE TO RELATED APPLICATIONS

This application claims the benefit of U.S. Provisional Application Ser. No. 62/753,337, filed 31 Oct. 2018, which is incorporated herein by reference in its entirety.

BACKGROUND OF THE INVENTION

The present disclosure relates generally to a millimeter-wave-radar-based electromagnetic, EM, apparatus, particularly to a wearable millimeter-wave-radar-based EM apparatus, and more particularly to a wearable millimeter-wave-radar-based-gesture-recognition EM apparatus.

Computing devices capable of gesture recognition have become increasingly common, with earlier gesture recognition devices being operable when the gestures were made to a surface of the device in question. A more recent gesture recognition device involves in-the-air gestures, which is disclosed in U.S. Pat. No. 9,921,660. A drawback to some existing gesture recognition devices relates to the size of the body portion of an actor performing the gesture, and the distance of the body portion from the device performing the gesture recognition. For example, in some existing gesture recognition devices, a small-body-portion gesture recognition (such as from one or two human fingers for example) requires that the small-body-portion of the actor be within millimeters of the device performing the gesture recognition, and in some other gesture recognition devices, gesture recognition at distances up to 20-30 centimeters from the device performing the gesture recognition requires that the gesture be performed by a large-body-portion of an actor (such as an human arm or a leg or a whole human body for example), or that the device performing the gesture recognition have a receiving antenna aperture large enough to receive the EM radiation reflections from the gesture being performed for recognition.

While existing gesture-recognition devices may be suitable for their intended purpose, the art of gesture recognition devices would be advanced with an antenna system that is capable of receiving discriminating gestures from a small-body-portion of an actor at distances up to 30 centimeters from the device performing the gesture recognition.

BRIEF DESCRIPTION OF THE INVENTION

In an embodiment, a wearable electromagnetic, EM, apparatus includes: at least one antenna operable in a millimeter-wave-radar-based, MWRB, application; at least one computer processor disposed in signal communication with the at least one antenna; an attachment system configured and adapted to attach to an actor; the at least one antenna and the at least one computer processor disposed in a supported relationship with the attachment system, such that the attachment system with the supported at least one antenna and the at least one computer processor at least partially forms a wearable apparatus that is wearable by the actor.

In an embodiment, an electromagnetic, EM, apparatus, includes: a millimeter-wave-radar-based-gesture-recognition, MWRBGR, system, having: at least one antenna operable in a millimeter-wave-radar-based, MWRB, application; at least one computer processor disposed in signal communication with the at least one antenna; the at least one antenna configured and adapted to transmit an EM radiation field and to receive EM radiation reflections from the EM radiation field, the EM radiation reflections based at least partially on a recognized gesture of an actor; the at least one computer processor being responsive to executable instructions which when executed by the at least one computer processor facilitates a particular operation based at least partially on the recognized gesture of the actor.

In an embodiment, a wearable electromagnetic, EM, apparatus, includes: at least one antenna operable in a millimeter-wave frequency, the at least one antenna comprising a dielectric resonator antenna, DRA, array; at least one computer processor disposed in signal communication with the at least one antenna; an attachment system configured and adapted to attach to an actor; the at least one antenna and the at least one computer processor disposed in a supported relationship with the attachment system, such that the attachment system with the supported at least one antenna and the at least one computer processor at least partially forms a wearable apparatus that is wearable by the actor.

In an embodiment, any one of the foregoing EM apparatus, wherein the at least one antenna is a DRA having: an electrically conductive ground structure; a plurality of volumes of dielectric materials disposed on the ground structure having N volumes, N being an integer equal to or greater than 3, disposed to form successive and sequential layered volumes V(i), i being an integer from 1 to N, wherein volume V(1) forms an innermost volume, wherein a successive volume V(i+1) forms a layered shell disposed over and at least partially embedding volume V(i), wherein volume V(N) at least partially embeds all volumes V(1) to V(N−1); and a signal feed disposed and structured to be electromagnetically coupled to one or more of the plurality of volumes of dielectric materials.

The above features and advantages and other features and advantages of the invention are readily apparent from the following detailed description of the invention when taken in connection with the accompanying drawings.

BRIEF DESCRIPTION OF THE DRAWINGS

Referring to the exemplary non-limiting drawings wherein like elements are numbered alike in the accompanying Figures:

FIG. 7 depicts an alternative form of a wearable version of the EM apparatus of FIG. 1, depicted as a wearable head apparatus, in accordance with an embodiment;

FIG. 8 depicts an alternative form of a wearable version of the EM apparatus of FIG. 1, depicted as another wearable head apparatus, in accordance with an embodiment;

FIG. 9 depicts an alternative form of a wearable version of the EM apparatus of FIG. 1, depicted as a wearable face apparatus, in accordance with an embodiment;

FIGS. 10A, 10B, and 10C, depict example gestures of a particular actor suitable for use in accordance with an embodiment;

DETAILED DESCRIPTION OF THE INVENTION

Although the following detailed description contains many specifics for the purposes of illustration, anyone of ordinary skill in the art will appreciate that many variations and alterations to the following details are within the scope of the appended claims. Accordingly, the following example embodiments are set forth without any loss of generality to, and without imposing limitations upon, the claimed invention disclosed herein.

An embodiment, as shown and described by the various figures and accompanying text, provides a millimeter-wave-radar-based, MWRB, electromagnetic, EM, apparatus, particularly a wearable MWRB EM apparatus, and more particularly a millimeter-wave-radar-based-gesture-recognition, MWRBGR, system.

Figure 1:
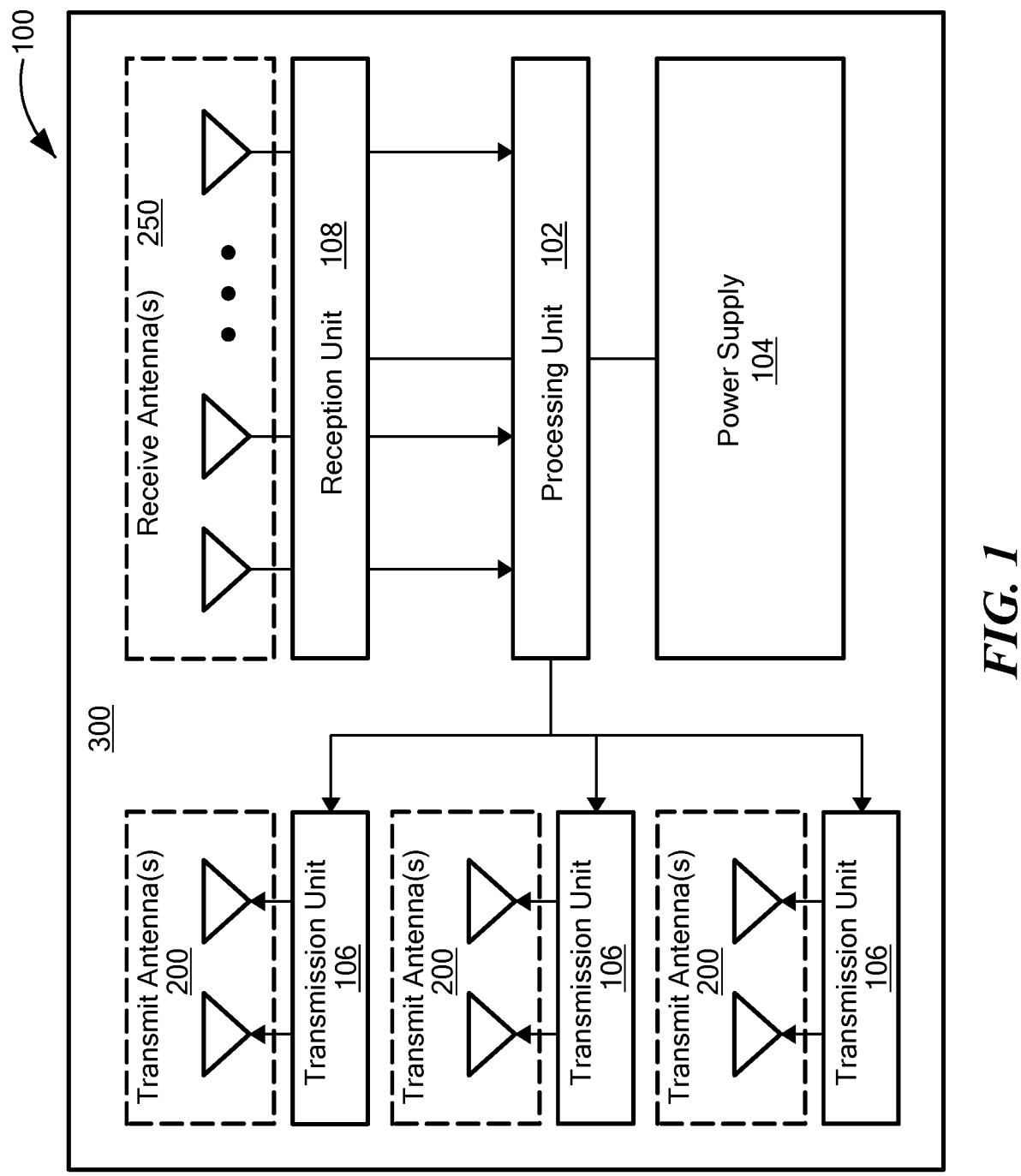
FIG. 1 depicts a block diagram representation of an EM apparatus that may be wearable by a particular actor, in accordance with an embodiment.

FIG. 1 depicts a block diagram representation of an EM apparatus 100 that may be wearable by a particular actor 400 (see subsequent figures for example), and may be operable as a gesture recognition system. In an embodiment, the EM apparatus 100 includes at least one antenna 200, 250 operable in a MWRB application, at least one computer processor 102 disposed in signal communication with the at least one antenna 200, 250, and an attachment system 300 configured and adapted to attach to the actor 400, wherein the at least one antenna 200, 250 and the at least one computer processor 102 are disposed in a supported relationship with the attachment system 300, such that the attachment system 300 with the supported at least one antenna 200, 250 and the at least one computer processor 102 at least partially forms a wearable apparatus 100 that is wearable by the actor 400. As used herein, the term actor refers to a particular mammal, or more particularly to a particular human, and the wearable EM apparatus 100 may be operable as a MWRBGR system that recognizes and is responsive to gestures performed by the actor 400. In an alternative embodiment, the EM apparatus 100 may be so configured and adapted as to not be worn by an actor, which will be described further herein below. In an embodiment, the EM apparatus 100 further includes a power supply 104 disposed in signal communication with the at least one computer processor 102, at least one transmission unit 106 disposed in signal communication with the at least one computer processor 102, and at least one reception unit 108 disposed in signal communication with the at least one computer processor 102. The at least one transmission unit 106 is disposed and configured in signal communication with the at least one antenna 200, which in an embodiment is at least one transmit (or transmitter) antenna 200, and the at least one reception unit 108 is disposed and configured in signal communication with the at least one antenna 250, which in an embodiment is at least one reception (or receiver) antenna 250.

In an embodiment, the at least one antenna 200, 250 is a plurality of antennas 200, 250 configured and adapted as a monostatic antenna to transmit an EM radiation field and to receive EM radiation reflections from the EM radiation field, wherein the EM radiation reflections are based at least partially on a recognized gesture of the actor 400, and the at least one computer processor 102 is responsive to executable instructions which when executed by the at least one computer processor 102 facilitates a particular operation based at least partially on the recognized gesture of the actor 400. In an embodiment, the monostatic antenna 200, 250 that is configured and adapted to receive EM radiation reflections has an effective EM aperture so dimensioned and configured as to enable resolution via the at least one computer processor 102 of the recognized gesture at a distance up to 30 cm from the EM apparatus 100.

In another embodiment, the at least one antenna 200, 250 is a plurality of antennas 200, 250 configured and adapted as a bistatic antenna having at least one first set of transmitter antennas 200 and at least one second set of receiver antennas 250, wherein the at least one first set of transmitter antennas 200 is configured and adapted to transmit an EM radiation field, and wherein the at least one second set of receiver antennas 250 is configured and adapted to receive EM radiation reflections from the EM radiation field, the EM radiation reflections being based at least partially on a recognized gesture of the actor 400, and wherein the at least one computer processor 102 is responsive to executable instructions which when executed by the at least one computer processor 102 facilitates a particular operation based at least partially on the recognized gesture of the actor 400. In an embodiment, the at least one second set of receiver antennas 250 has an effective EM aperture so dimensioned and configured as to enable resolution via the at least one computer processor 102 of the recognized gesture at a distance up to 30 cm from the EM apparatus 100.

In an embodiment, the at least one antenna 200, 250 is operable in a frequency range of: equal to or greater than 10 GHz and equal to or less than 400 GHz; or, equal to or greater than 30 GHz and equal to or less than 300 GHz; or, equal to or greater than 50 GHz and equal to or less than 100 GHz; or, equal to or greater than 54 GHz and equal to or less than 66 GHz.

Reference is now made to FIGS. 2-9, which depict alternative forms of a wearable version of the EM apparatus 100 that is wearable by an actor 400. For example, in an embodiment the wearable EM apparatus 100 is in the form of: a wearable wrist apparatus 110 (represented by FIG. 2 for example); a bracelet 110 (represented by FIG. 2 for example); a wrist watch 110 (represented by FIG. 2 for example); a wearable neck apparatus 112 (represented by FIGS. 3-5 for example); a necklace 114 (represented by FIG. 3 for example); a neck apparel 116 (represented by FIGS. 4-5 for example); a wearable clothing apparatus 118 (represented by FIGS. 5-6 for example); a brooch 118 (represented by FIG. 6 for example); a wearable head apparatus 120 (represented by FIGS. 7-9 for example); a headset 122 (represented by FIG. 7 for example); a helmet 124 (represented by FIG. 8 for example); a wearable face apparatus 126 (represented by FIG. 9 for example); an eyeglass 126 (represented by FIG. 9 for example); or, a pair of eyeglasses 126 (represented by FIG. 9 for example).

In an embodiment, the attachment system 300 depicted in FIG. 1 may be a wristband 302 (see FIG. 2 for example), or a chain 304 (see FIG. 3 for example), or a catch 306 (see FIG. 4 for example), or a surface 308 of a wearable article (see FIG. 5 for example), or a pin 310 (see FIG. 6 for example), or a head band 312 (see FIG. 7 for example), or a helmet 314 (see FIG. 8 for example), or a facial support member 316, such as eyeglass arms (see FIG. 9 for example), or any other structural member suitable for a purpose disclosed herein.

Figure 2:
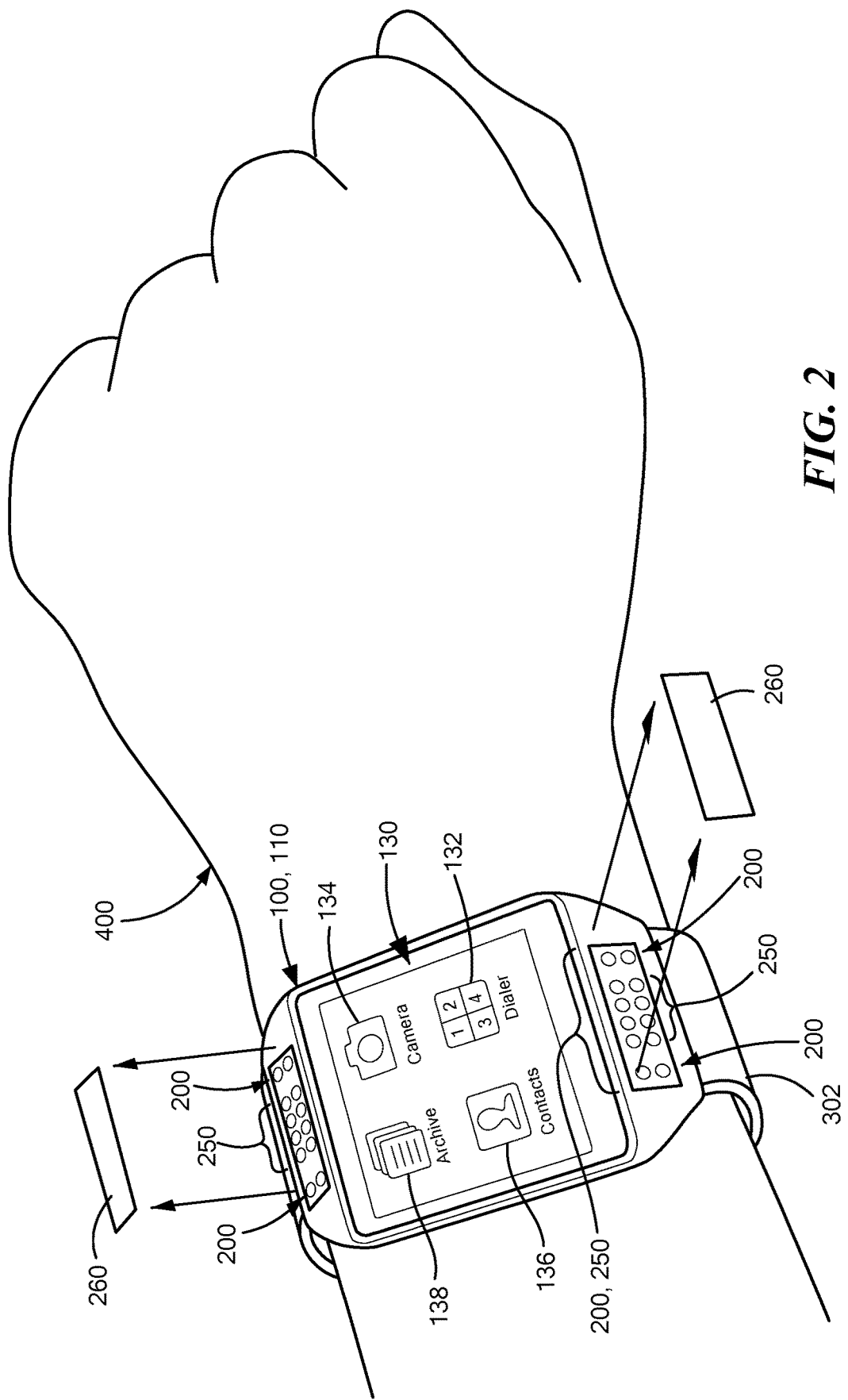
FIG. 2 depicts an alternative form of a wearable version of the EM apparatus of FIG. 1, depicted as a wearable wrist apparatus, in accordance with an embodiment.
Figure 3:
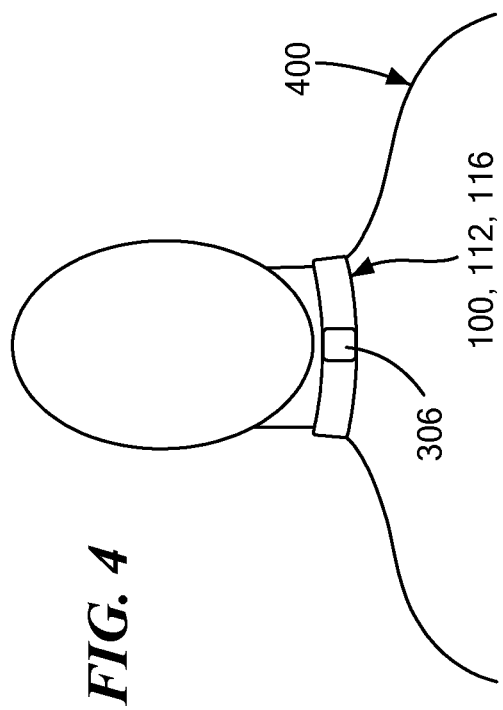
FIG. 3 depicts an alternative form of a wearable version of the EM apparatus of FIG. 1, depicted as a wearable neck apparatus, in accordance with an embodiment.
Figure 4:
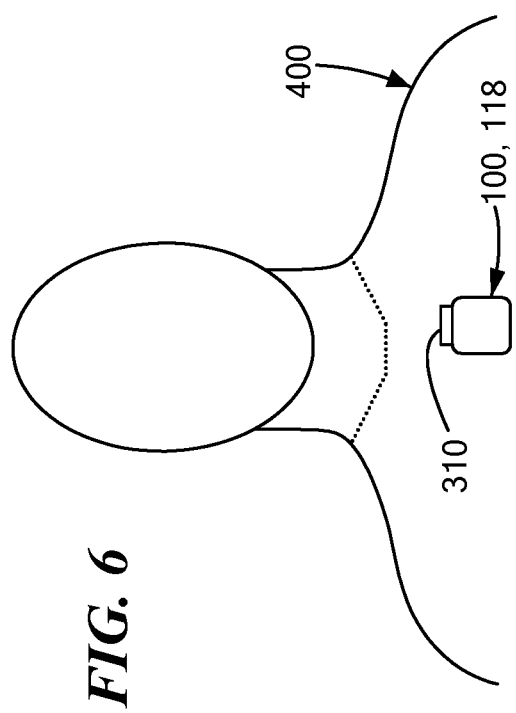
FIG. 4 depicts an alternative form of a wearable version of the EM apparatus of FIG. 1, depicted as another wearable neck apparatus, in accordance with an embodiment.
Figure 5:
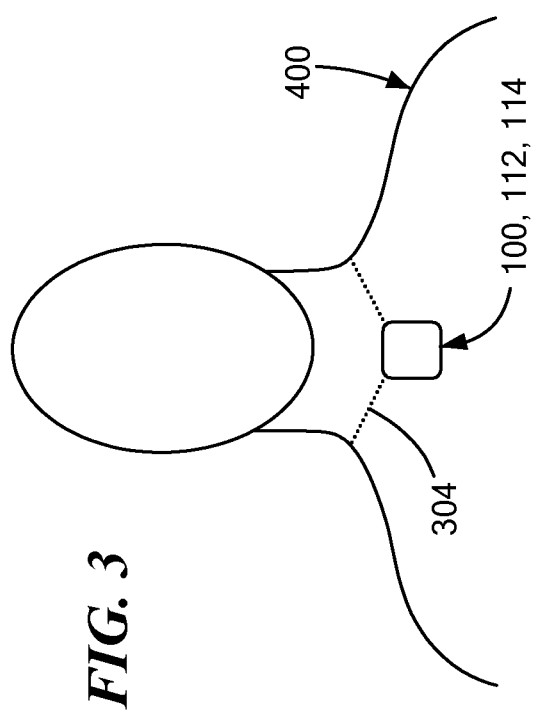
FIG. 5 depicts an alternative form of a wearable version of the EM apparatus of FIG. 1, depicted as yet another wearable neck apparatus, in accordance with an embodiment.
Figure 6:
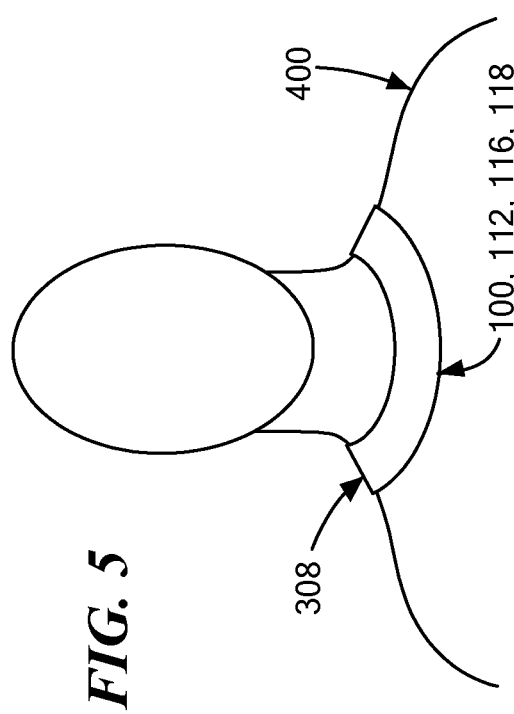
FIG. 6 depicts an alternative form of a wearable version of the EM apparatus of FIG. 1, depicted as a wearable clothing apparatus, in accordance with an embodiment.

In an embodiment wherein the EM apparatus 100 forms at least part of the wearable wrist apparatus 110, with reference to FIG. 2, the at least one antenna 200, 250 may be disposed on the wristband 302 of the wrist apparatus 110 proximate but not integral with a display 130 portion of the wrist apparatus 110. In an embodiment, the at least one antenna 200, 250 may comprise arrays of the at least one antenna 200, 250. For example and as depicted in FIG. 2, the at least one antenna 200, 250 may comprise a plurality of antennas arranged in respective arrays of antennas, and more specifically, the plurality of transmitter antennas 200 may comprise two sets of transmitter antennas 200 arranged in an array on each side of the display 130 (two sets of four transmitter antennas 200 depicted in FIG. 2, for example), and the plurality of receiver antennas 250 may comprise two sets of receiver antennas 250 arranged in an array on each side of the display 130 (two sets of eight receiver antennas 250 depicted in FIG. 2, for example). Protective covers 260 may be utilized to protect the at least one antenna 200, 250, which are attached to the wrist apparatus 110 in any manner suitable for a purpose disclosed herein. As depicted in FIG. 2, the display 130 of the wrist apparatus 110 depicts example icons 132, 134, 136, 138, which when activated, via touch or tactile sensors for example, facilitate a particular action, such as: dialing a telephone number using a telephone configured and adapted to be in signal communication with the EM apparatus 100 (icon 132 for example); accepting an incoming telephone call using a telephone configured and adapted to be in signal communication with the EM apparatus 100 (icon 132 for example); raising or lowering a speaker volume of a telephone configured and adapted to be in signal communication with the EM apparatus 100 (icon 132 for example); taking a photograph using a camera configured and adapted to be in signal communication with the EM apparatus 100 (icon 134 for example); opening an electronic contact file using an electronic contact list configured and adapted to be in signal communication with the EM apparatus 100 (icon 136 for example); or, saving or accessing archived information in a non-transitory computer readable medium configured and adapted to be in signal communication with the EM apparatus 100 (icon 138 for example). While only four icons 132, 134, 136, 138 are depicted in FIG. 2 and associated with certain functions, it will be appreciated that this is for illustration purposes only, and that other icons for other functions may also be implemented, such as for example: measuring a blood pressure of the actor and alerting the actor with the measured value in an event where the EM apparatus 100 is worn by the actor and the blood pressure of the actor is equal to or greater than a first particular value, or is equal to or less than a second particular value; measuring a bone density of the actor and alerting the actor with the measured value in an event where the EM apparatus 100 is worn by the actor and the bone density of the actor is equal to or less than a particular value; measuring a heart rate of the actor and alerting the actor with the measured value in an event where the EM apparatus 100 is worn by the actor and the heart rate of the actor is equal to or greater than a first particular value, or is equal to or less than a second particular value; or, interpreting the recognized gesture as a rapid movement suggestive of a fall and sending an alert communication to a particular recipient other than the actor in an event where the EM apparatus 100 is worn by the actor. In an embodiment, one or more of the aforementioned functions may be performed by any EM apparatus 100 as disclosed herein, and further described herein below.

In an embodiment wherein the EM apparatus 100 forms at least part of the wearable neck apparatus 112, the necklace 114, the neck apparel 116, the wearable clothing apparatus 118, or the brooch 118, and the at least one antenna 200, 250 is disposed proximate a surface of the wearable neck apparatus 112, the necklace 114, the neck apparel 116, the wearable clothing apparatus 118, or the brooch 118, and faces substantially toward the actor 400.

In an embodiment wherein the EM apparatus 100 forms at least part of the wearable head apparatus 120, the headset 122, or the helmet 124, and the at least one antenna 200, 250 is disposed proximate a surface of the wearable head apparatus 120, the headset 122, or the helmet 124, and faces substantially away from the actor 400.

In an embodiment wherein the EM apparatus 100 forms at least part of the wearable face apparatus 126, the eyeglass 126, or the pair of eyeglasses 126, and the at least one antenna 200, 250 is disposed proximate a surface of the wearable face apparatus 126, the eyeglass 126, or the pair of eyeglasses 126, and faces substantially away from the actor 400. In an embodiment, the at least one antenna 200, 250 is disposed proximate but not integral with a lens portion 130 of the eye glass or the pair of eyeglasses 126.

With reference now to FIGS. 10A, 10B, 10C, an example gesture of the actor 400 may be in the form of hand or finger gestures, with FIG. 10A being representative of an open-palm hand sideways gesture 402, FIG. 10B being representative of a fisted-hand vertical gesture 404, and FIG. 10C being representative of an open-to-closed-palm finger gesture 406, with all gestures 402, 404, 406 being performed in the EM radiation field 450, with corresponding EM radiation reflections 412, 414, 416 therefrom being based at least partially on the recognized gesture of the actor 400, and where the EM radiation reflections 412, 414, 416 are received by the at least one receive antenna 250. While FIGS. 10A, 10B, 10C, depict only a few gestures from the actor 400, it will be appreciated that this is for illustration purposes only, and that one skilled in the art would appreciate that other non-illustrated gestures are not only conceivable, but would also be contemplated to fall within an ambit of the claimed invention.

In an embodiment, the at least one computer processor 102 is responsive to executable instructions which when executed on the at least one computer processor 102 facilitates a particular operation that is based at least partially on the recognized gesture of the actor 400, wherein the particular operation may include any one of: dialing a telephone number using a telephone configured and adapted to be in signal communication with the EM apparatus 100; accepting an incoming telephone call using a telephone configured and adapted to be in signal communication with the EM apparatus 100; raising or lowering a speaker volume of a telephone configured and adapted to be in signal communication with the EM apparatus 100; taking a photograph using a camera configured and adapted to be in signal communication with the EM apparatus 100; opening an electronic contact file using an electronic contact list configured and adapted to be in signal communication with the EM apparatus 100; saving or accessing archived information in a non-transitory computer readable medium configured and adapted to be in signal communication with the EM apparatus 100; measuring a blood pressure of the actor and alerting the actor with the measured value in an event where the EM apparatus 100 is worn by the actor 400 and the blood pressure of the actor 400 is equal to or greater than a first particular value, or is equal to or less than a second particular value; measuring a bone density of the actor 400 and alerting the actor 400 with the measured value in an event where the EM apparatus 100 is worn by the actor 400 and the bone density of the actor 400 is equal to or less than a particular value; measuring a heart rate of the actor 400 and alerting the actor 400 with the measured value in an event where the EM apparatus 100 is worn by the actor 400 and the heart rate of the actor 400 is equal to or greater than a first particular value, or is equal to or less than a second particular value; or, interpreting the recognized gesture as a rapid movement suggestive of a fall of the actor 400 and sending an alert communication to a particular recipient other than the actor 400 in an event where the EM apparatus 100 is worn by the actor 400.

Figure 11:
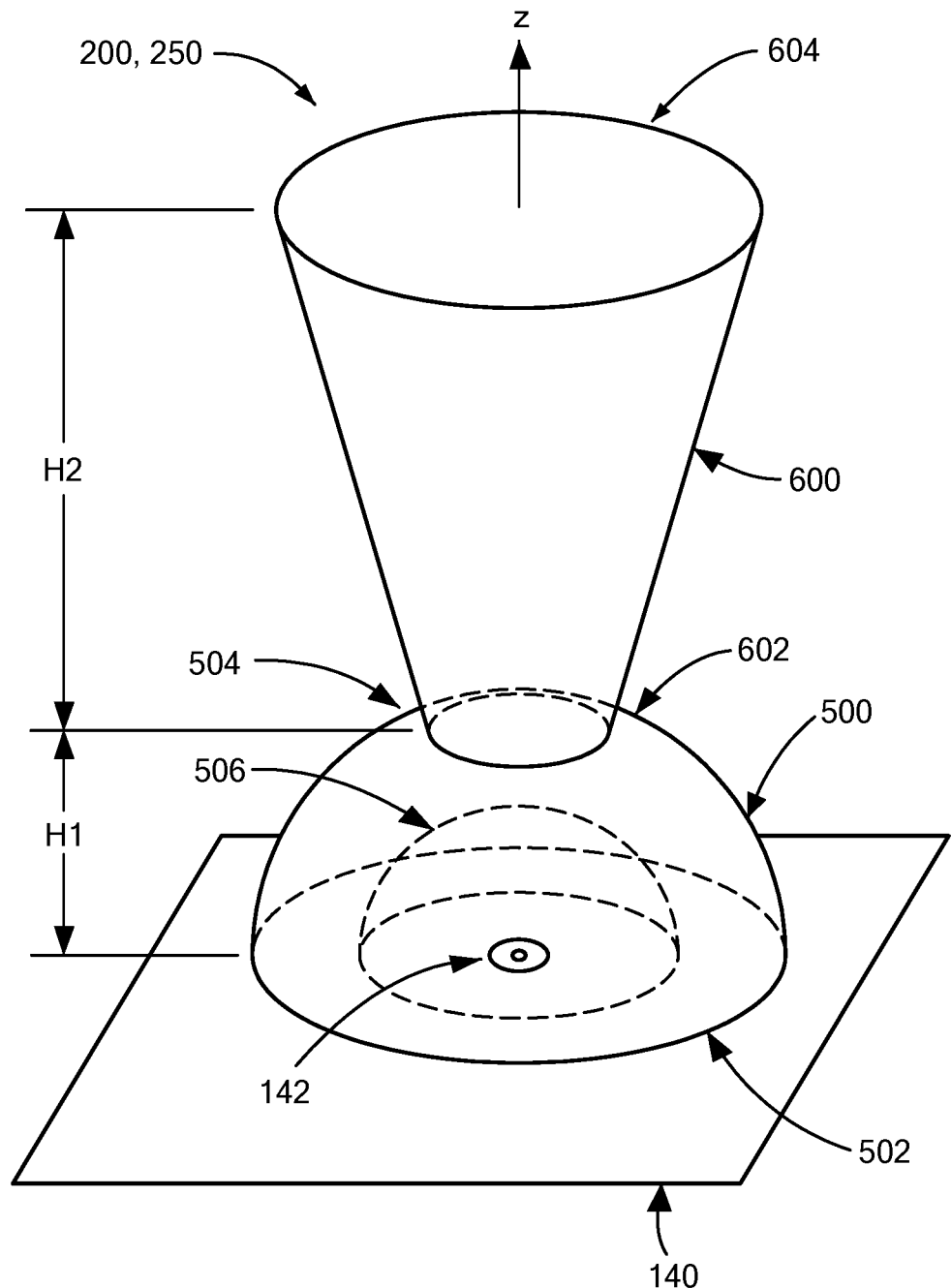
FIG. 11 depicts an example antenna in the form of a dielectric resonator antenna, DRA, that may or may not include a dielectric lens or a dielectric waveguide, in accordance with an embodiment.
Figure 12A:
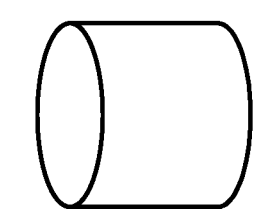
FIGS. 12A, 12B, 12C, 12D, 12E, 12F, 12G, 12H, 12I, 12J, and 12K, depict alternative three-dimensional shapes suitable for the DRA, and/or the lens or waveguide, depicted in FIG. 11, in accordance with an embodiment.
Figure 12B:
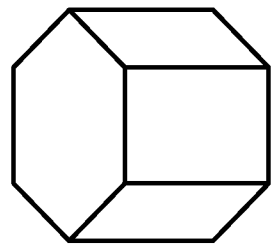
Figure 12C:
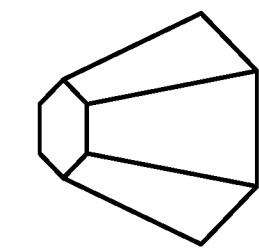
Figure 12D:
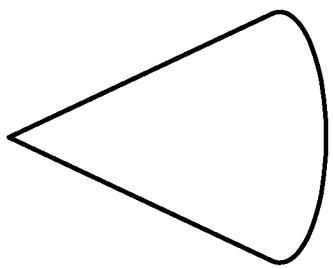
Figure 12E:
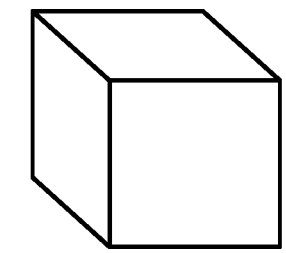
Figure 12F:
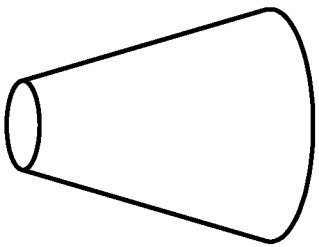
Figure 12G:
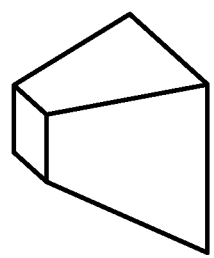
Figure 12H:
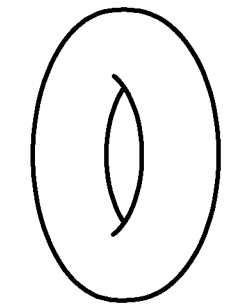
Figure 12I:
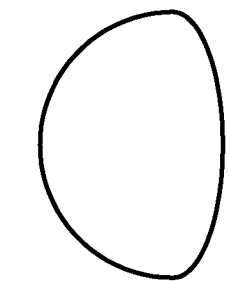
Figure 12J:
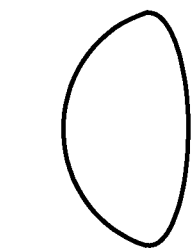
Figure 12K:
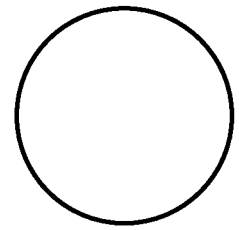
Figure 13C:
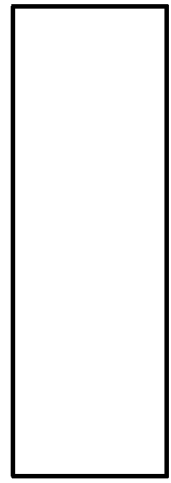
FIGS. 13A, 13B, 13C, 13D, and 13E, depict alternative two-dimensional cross section shapes of the three-dimensional shapes of FIGS. 12A-12K, in accordance with an embodiment.
Figure 13E:
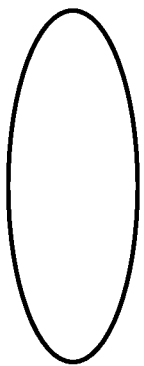
Figure 13B:
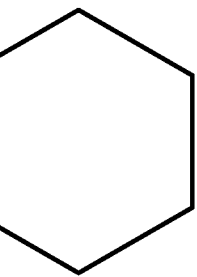
Figure 13D:
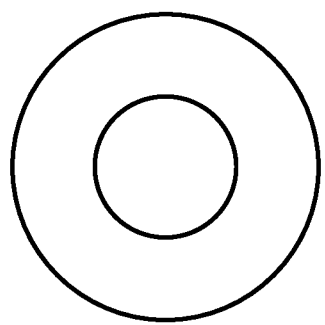
Figure 13A:
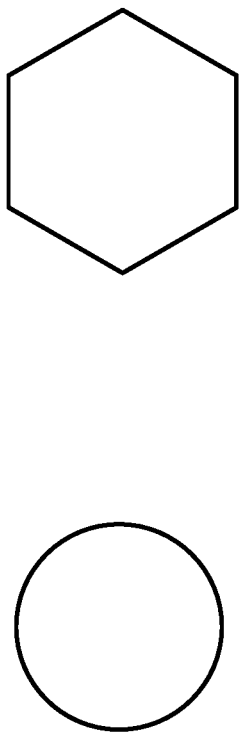

In an embodiment, and with reference now to FIG. 11, the at least one antenna 200, 250 is at least one dielectric resonator antenna, DRA, 500 that may or may not include a dielectric lens or waveguide 600 configured and disposed in EM communication with the DRA 500. In an embodiment, the dielectric lens 600 is a Luneburg lens having a dielectric material with a dielectric constant that varies from one portion of the dielectric lens 600 to another portion of the dielectric lens 600, and in an embodiment more specifically varies decreasingly from an inner portion of the dielectric lens 600 to an outer surface of the dielectric lens 600. That said, in another embodiment the dielectric lens 600 is not a Luneburg lens per se, but may still be a lens formed of a dielectric material composed of different dielectric constants. In an embodiment, the DRA 500 may alternatively be referred to as a first dielectric portion, 1DP, and the lens or waveguide 600 may alternatively be referred to as a second dielectric portion, 2DP. In an embodiment, the 1DP 500 has a proximal end 502 and a distal end 504, and the 2DP 600 has a proximal end 602 and a distal end 604, where the proximal end 602 of the 2DP 600 is disposed proximate and in EM communication with the distal end 504 of the 1DP 500. In an embodiment, the proximal end 602 of the 2DP 600 is disposed in direct contact with the distal end 504 of the 1DP 500. In an embodiment, the 1DP 500 is disposed on an electrically conductive ground structure 140.

In an embodiment, the 1DP 500 may be a plurality of volumes of dielectric materials disposed on the ground structure 140, wherein the plurality of volumes of dielectric materials comprise N volumes, N being an integer equal to or greater than 3, disposed to form successive and sequential layered volumes V(i), i being an integer from 1 to N, wherein volume V(1) forms an innermost volume, wherein a successive volume V(i+1) forms a layered shell disposed over and at least partially embedding volume V(i), wherein volume V(N) at least partially embeds all volumes V(1) to V(N-1). The dashed line form 506 depicted in FIG. 11 is representative of any number of the plurality of volumes of dielectric materials V(N) as disclosed herein. In an embodiment, an electrical signal feed 142 is disposed and structured to be electromagnetically coupled to one or more of the plurality of volumes of dielectric materials. While FIG. 11 depicts the electrical signal feed 142 as being representative of a coaxial cable, it will be appreciated that this is for illustration purposes only, and that the signal feed 142 may be any kind of signal feed suitable for a purpose disclosed herein, such as a copper wire, a coaxial cable, a microstrip (e.g., with slotted aperture), a stripline (e.g., with slotted aperture), a waveguide, a surface integrated waveguide, a substrate integrated waveguide, or a conductive ink, for example, that is electromagnetically coupled to the respective 1DP 500. Furthermore, while FIG. 11 depicts the signal feed 142 being disposed in EM signal communication with the innermost volume V(1), it will be appreciated that this is for illustration purposes only, and that the signal feed 142 may be disposed in EM signal communication with any volume V(N) consistent with a purpose disclosed herein, such as but not limited to volume V(2) for example.

In an embodiment, volume V(1) comprises air. In an embodiment, volume V(2) comprises a dielectric material other than air. In an embodiment, volume V(N) comprises air. In an embodiment, volume V(N) comprises a dielectric material other than air.

As disclosed herein and with reference to all of the foregoing, an EM apparatus 100 may comprise a 1DP 500 in the form of a dielectric resonator antenna, DRA, for example, and a 2DP 600 in the form of: a dielectric lens, or any other dielectric element that forms an EM far field beam shaper, for example; or, a dielectric waveguide, or any other dielectric element that forms an EM near field radiation conduit, for example. As disclosed herein, and as will be appreciated by one skilled in the art, the 1DP and the 2DP are distinguishable over each other in that the 1DP is structurally configured and adapted to have an EM resonant mode that coincides with an EM frequency of an electrical signal source that is electromagnetically coupled to the 1DP, and the 2DP is structurally configured and adapted to: in the case of a dielectric EM far field beam shaper, serve to affect the EM far field radiation pattern originating from the 1DP when excited without itself having a resonant mode that matches the EM frequency of the electrical signal source; or, in the case of a dielectric EM near field radiation conduit, serve to propagate the EM near field emission originating from the 1DP when excited with little or no EM signal loss along the length of the 2DP. As disclosed herein, the phrase electromagnetically coupled is a term of art that refers to an intentional transfer of EM energy from one location to another without necessarily involving physical contact between the two locations, and in reference to an embodiment disclosed herein more particularly refers to an interaction between an electrical signal source having an EM frequency that coincides with an EM resonant mode of the associated 1DP and/or 1DP combined with the 2DP. In an embodiment, the electromagnetically coupled arrangement is selected such that greater than 50% of the resonant mode EM energy in the near field is present within the 1DP for a selected operating free space wavelength associated with the EM apparatus. In some embodiments, the height H2 of the 2DP is greater than the height of the 1DP (e.g., the height of the 2DP is greater than 1.5 times the height of the 1DP, or the height of the 2DP is greater than 2 times the height of the 1DP, or the height of the 2DP is greater than 3 times the height of the 1DP). In some embodiments, the average dielectric constant of the 2DP is less than the average dielectric constant of the 1DP (e.g., the average dielectric constant of the 2DP is less than 0.5 the average dielectric constant of the 1DP, or the average dielectric constant of the 2DP is less than 0.4 the average dielectric constant of the 1DP, or the average dielectric constant of the 2DP is less than 0.3 the average dielectric constant of the 1DP). In some embodiments, the 2DP has axial symmetry around a specified axis. In some embodiments, the 2DP has axial symmetry around an axis that is normal to an electrical ground plane surface on which the 1DP is disposed.

In an embodiment, and with reference to FIGS. 12A-12K, any dielectric structure 500, 600 disclosed herein may have a three-dimensional form in the shape of a cylinder (FIG. 12A), a polygon box (FIG. 12B) a tapered polygon box (FIG. 12C), a cone (FIG. 12D), a cube (FIG. 12E), a truncated cone (FIG. 12F), a square pyramid (FIG. 12G), a toroid (FIG. 12H), a dome (FIG. 12I), an elongated dome (FIG. 12J), a sphere (FIG. 12K), or any other three-dimensional form suitable for a purpose disclosed herein. Referring now to FIGS. 13A-13E, such shapes can have can have a z-axis cross section in the shape of a circle FIG. 13A), a polygon (FIG. 13B), a rectangle (FIG. 13C), a ring (FIG. 13D), an ellipsoid (FIG. 13E), or any other shape suitable for a purpose disclosed herein. In addition, the shape can depend on the polymer used, the desired dielectric gradient, and the desired mechanical and electrical properties.

Figure 14:
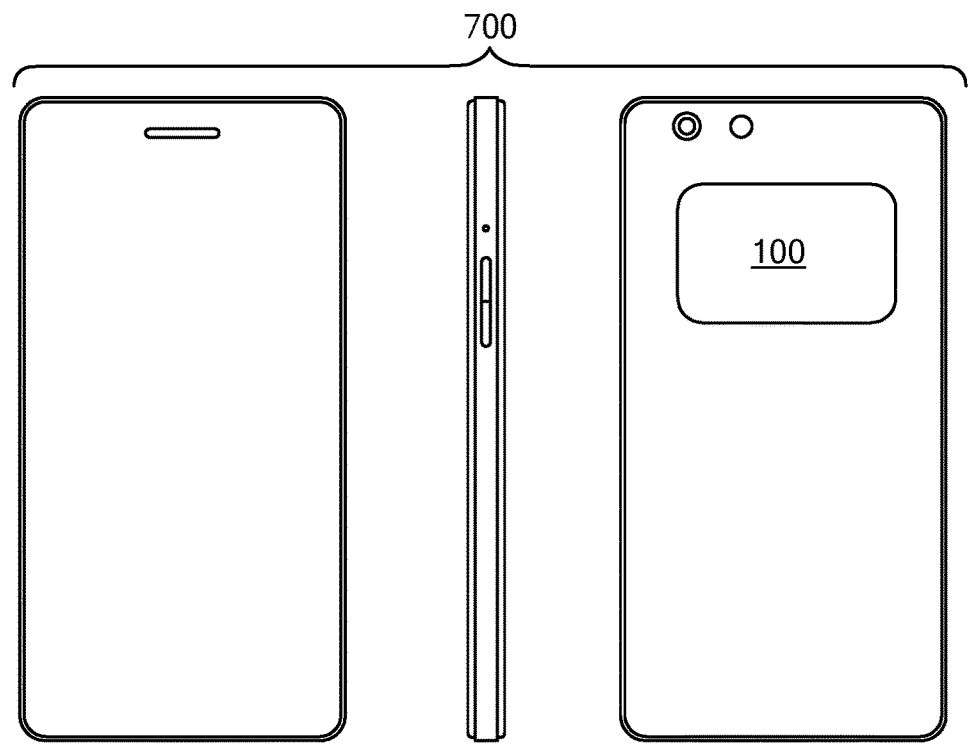
FIG. 14 depicts an example hand-held mobile communication device having an EM apparatus, in accordance with an embodiment.
Figure 15:
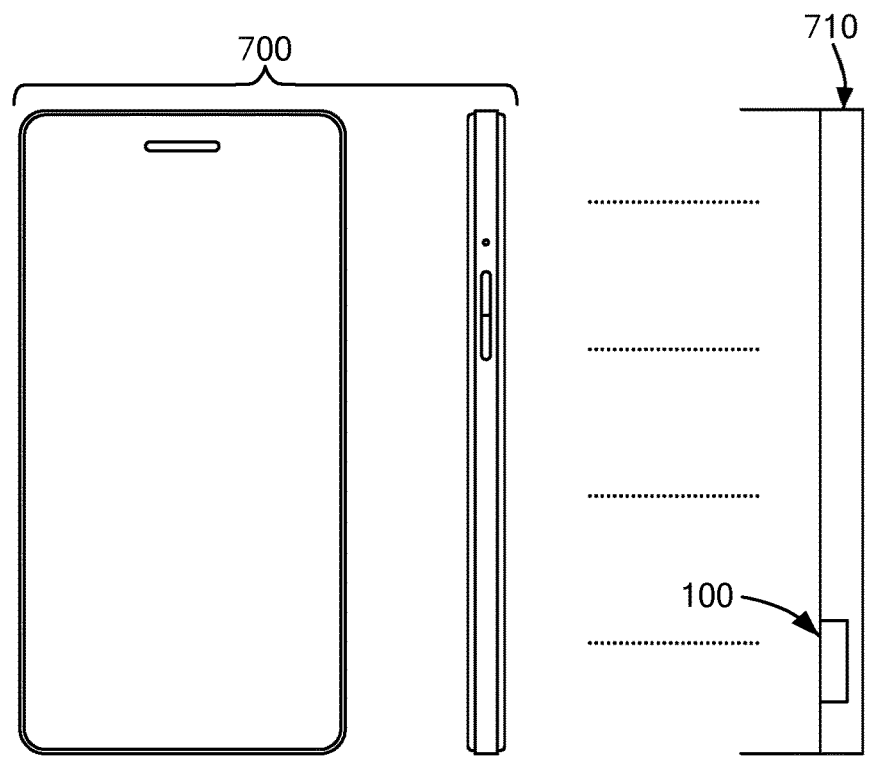
FIG. 15 depicts another example hand-held mobile communication device having an EM apparatus, in accordance with an embodiment.
Figure 16A:
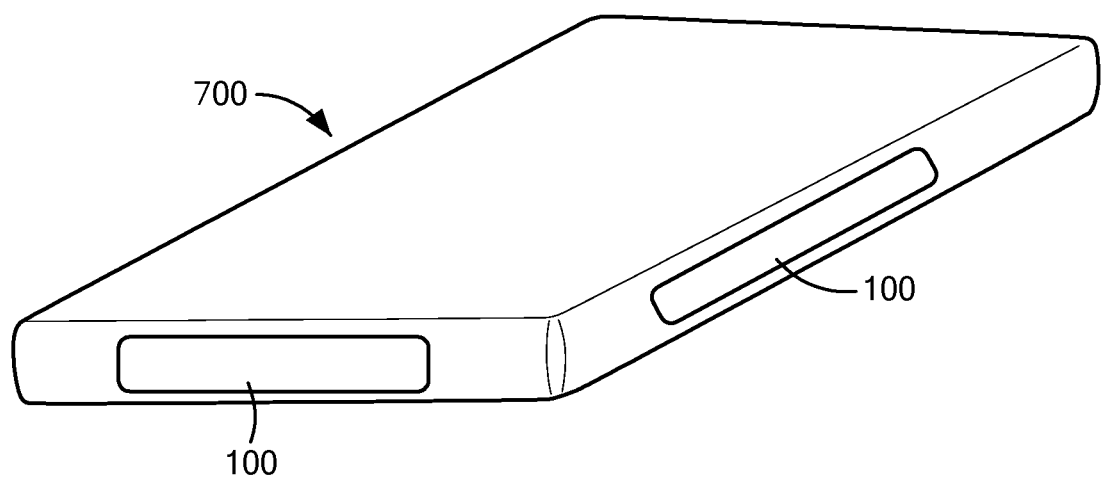
FIGS. 16A and 16B depict yet another example hand-held mobile communication device having an EM apparatus, in accordance with an embodiment.
Figure 16B:
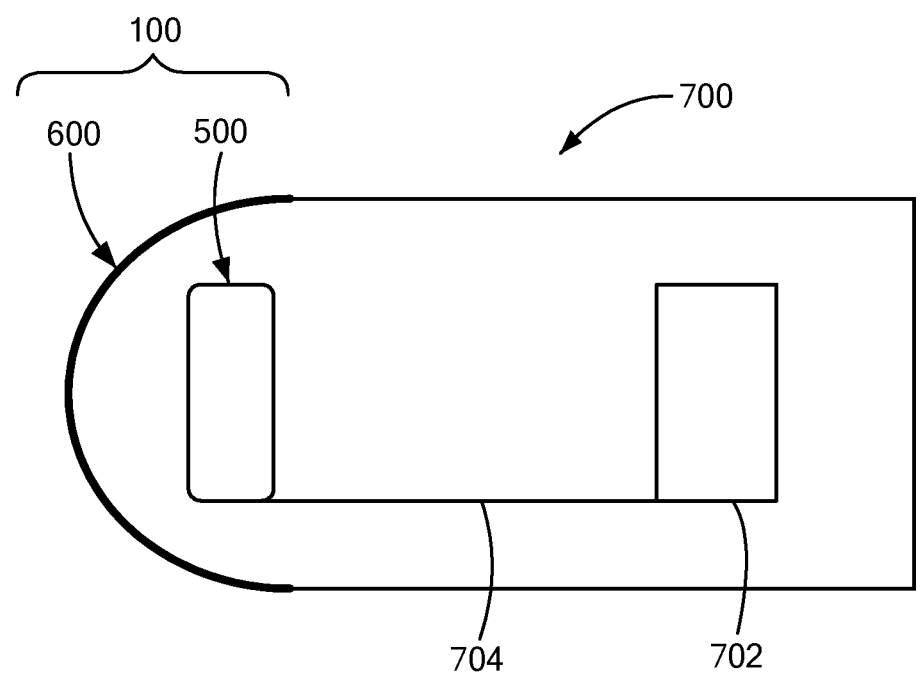

In an embodiment, and with reference to FIGS. 14-16B, an EM apparatus 100 useful in a MWRB application, or MWRBGR system, as disclosed herein, may be integrated on a hand-held mobile device 700, such as a cell phone for example. In an embodiment, the EM apparatus 100 may be integrated on a back surface of the hand-held mobile communication device 700, as depicted in FIG. 14 for example, and may be used as an antenna array for communication and/or radar for gesture recognition for example. In an embodiment, the gesture recognition may be recognition of a non-contact finger gesture of an actor 400 (see FIGS. 10A-10C for example) that would facilitate the taking of a picture via the onboard camera of the hand-held mobile communication device 700 without the need to include a dedicated button or increased size for performing such action. In an embodiment, the EM apparatus 100 may be integrated on an antenna extender and signal enhancer 710 for boosting a signal of the hand-held mobile communication device 700, as depicted in FIG. 15 for example. As with the hand-held mobile communication device 700 of FIG. 14, the antenna extender and signal enhancer 710 of FIG. 15 may also be used as an antenna array for communication and/or radar for gesture recognition for example. In an embodiment, the EM apparatus 100 may be integrated on outer edges of the hand-held mobile communication device 700, as depicted in FIG. 16A for example, and may also be used as an antenna array for communication and/or radar for gesture recognition for example. The array of antennas 200, 250 of the EM apparatus 100 may be disposed perpendicular to an outer edge of the hand-held mobile communication device 700 to maintain a sleek and thin design. In an embodiment, the gesture recognition may be recognition of a non-contact finger gesture of an actor 400 (see FIGS. 10A-10C for example) that would facilitate an adjustment of volume on the hand-held mobile communication device 700 without the need to include up/down dedicated buttons or increased size for performing such action. With reference to FIG. 16B, which depicts a block diagram representation of a horizontal cross section of the hand-held mobile communication device 700 of FIG. 16A, an embodiment may include a lens (or plurality of lenses) 600 disposed at an outer edge of the hand-held mobile communication device 700, where the lens 600 is disposed in EM communication with the plurality of antennas (or DRAs) 500, and the antennas 500 are configured and disposed to be in signal communication with other electronic systems 702 of the hand-held mobile communication device 700 via a flex board 704, or via any other means suitable for a purpose disclosed herein.

Figures 17A, 17B:
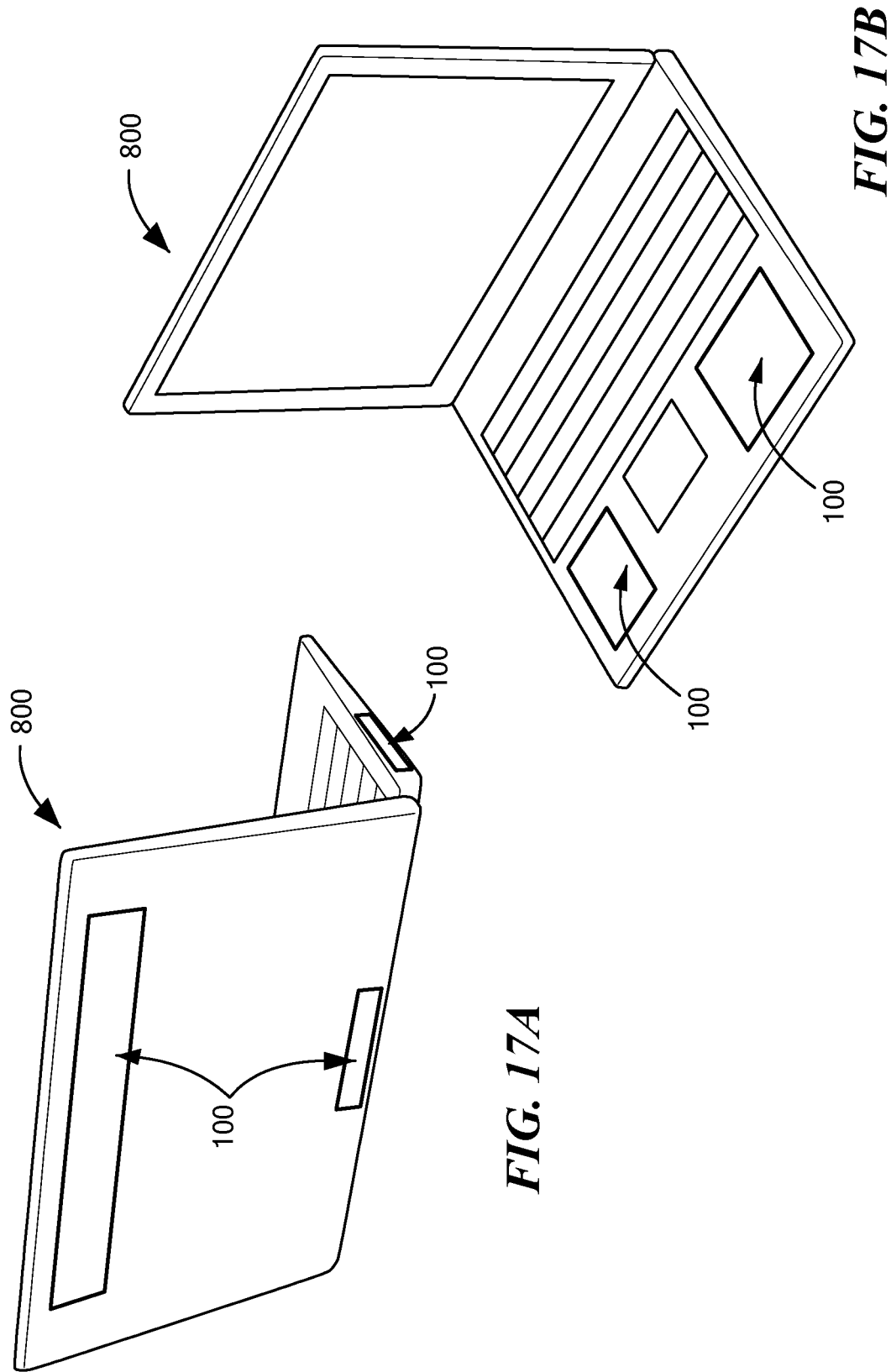
FIGS. 17A and 17B depict an example laptop computer having an EM apparatus, in accordance with an embodiment.

In an embodiment, and with reference to FIGS. 17A-17B, the EM apparatus 100 useful in a MWRB application, or MWRBGR system, as disclosed herein, may be integrated on a laptop computer 800. In an embodiment, the EM apparatus 100 may be integrated on a back surface or side surface of the laptop computer 800 as depicted in FIG. 17A for example, or may be integrated on an open front surface of the laptop computer 800 as depicted in FIG. 17B for example. In an embodiment, the gesture recognition may be recognition of a non-contact finger or hand gesture of an actor 400 (see FIGS. 10A-10C for example) that would facilitate various short-cut responses from the laptop computer 800, such as a change to which program is active on the laptop computer 800, or setting the laptop computer 800 in sleep mode, or dimming the screen when a presence of a user/actor 400 is not detected, without the need to include dedicated buttons or increased size for performing such action(s).

Figure 18:
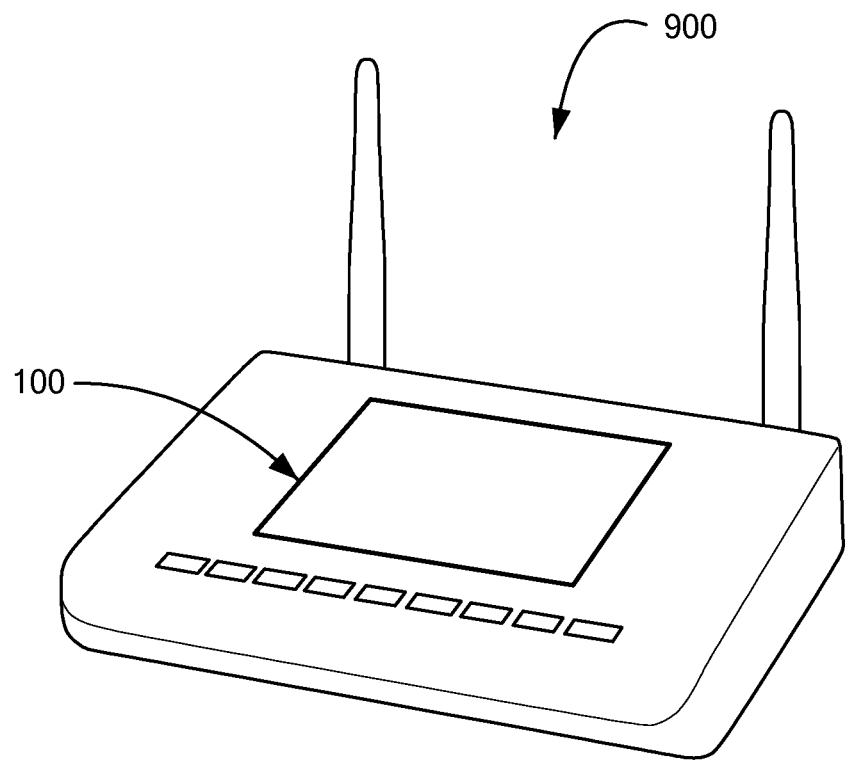
FIG. 18 depicts an example network extender having an EM apparatus, in accordance with an embodiment.

In an embodiment, and with reference to FIG. 18, the EM apparatus 100 useful in a MWRB application, or MWRBGR system, as disclosed herein, may be integrated on a network extender 900, where the array of antennas 200, 250 may be used to transmit and receive data in a building, office space, or residential space, to extend wifi connections, and where the size of the array of antennas 200, 250 can reduce or eliminate the height of existing antennas while offering an efficient way to expand signal range with a reduced overall height profile.

In an embodiment and with respect to all of the foregoing, any EM apparatus 100 as disclosed herein may be configured and disposed in signal communication with and form at least part of an extended reality system. As used herein, the term extended reality (XR or Cross Reality) is a term intended to refer to all real-and-virtual combined environments and human-machine interactions generated by computer technology and wearables, and includes representative forms such as augmented reality (AR), augmented virtuality (AV), and virtual reality (VR), and also extends into the areas interpolated among them.

While certain combinations of individual features have been described and illustrated herein, it will be appreciated that these certain combinations of features are for illustration purposes only and that any combination of any of such individual features may be employed in accordance with an embodiment, whether or not such combination is explicitly illustrated, and consistent with the disclosure herein. Any and all such combinations of features as disclosed herein are contemplated herein, are considered to be within the understanding of one skilled in the art when considering the application as a whole, and are considered to be within the scope of the appended claims in a manner that would be understood by one skilled in the art.

An embodiment as disclosed herein may be embodied in the form of computer-implemented processes and apparatuses for practicing those processes. In an embodiment, an apparatus for practicing those processes may be a control module, which may be a processor-implemented module or a module implemented by a computer processor, and may include a microprocessor, an ASIC, or software on a microprocessor. An embodiment as disclosed herein may also be embodied in the form of a computer program product having computer program code containing instructions embodied in a non-transitory tangible media, such as floppy diskettes, CD-ROMs, hard drives, USB (universal serial bus) drives, or any other computer readable storage medium, such as random access memory (RAM), read only memory (ROM), erasable programmable read only memory (EPROM), electrically erasable programmable read only memory (EEPROM), or flash memory, for example, wherein, when the computer program code is loaded into and executed by a computer, the computer becomes an apparatus for practicing an embodiment. An embodiment as disclosed herein may also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein when the computer program code is loaded into and executed by a computer, the computer becomes an apparatus for practicing an embodiment. When implemented on a general-purpose microprocessor, the computer program code segments configure the microprocessor to create specific logic circuits. A technical effect of the executable instructions is to recognize a gesture of an actor and facilitate a responsive action in connection therewith.

In view of all of the foregoing, it will be understood by one skilled in the art that embodiments disclosed herein may be useful in antenna arrays for short-range radar, such as millimeter-wave radar, that is useful in gesture recognition systems, where the benefits over existing antennas may include: broad bandwidth resulting in increased depth resolution, and/or increased efficiency resulting in increased battery life and/or increased detection range. Other embodiments disclosed herein may be useful in antenna arrays for millimeter-wave communication, where the benefits over existing antennas may include: broad bandwidth resulting in increased data range (such as in the 60 GHZ band for example), and/or increased efficiency resulting in increased battery life and/or increased communication range.

As disclosed herein, millimeter-wave antennas, and particularly millimeter-wave DRA arrays, may be integrated into, but are not limited to, wearable and mobile devices that would enhance the interaction of a particular actor with the device. With respect to gesture recognition, it is contemplated that such integration may offer one or more of the following advantages: allow a more natural interaction with the device that would promote freedom from graphical user interface screens; offer high efficiency and increased sensitivity that would reduce the need for close proximity action for the desired gesture recognition; limit the need for repeated and repetitive interactions with a graphical user interface screen; allow the use of under-utilized areas or unconventional locations such as an exposed edge of a device, to enhance the device's performance, in view of the small size of the individual DRAs; provide an increased radar aperture size resulting in a cross-range resolution that can resolve finger gestures of an actor at a greater distance than existing smaller aperture (for example, with 60 GHz millimeter-waves, an aperture of about 20 centimeters (cm) can resolve 1 cm shapes (e.g., fingers) at a distance up to about 30 cm, while an aperture of about 2 cm can resolve 1 cm shapes at a distance only up to about 3 cm); may be used as a biosensor that can track internal body responses such as blood pressure, glucose levels, bone density, and the like; offers flexibility to operate in a standalone unit or function as a full system that has sensors spread out and integrated with a central processing unit, such as where a wrist watch, a necklace, or any other communication device disclosed herein, all report back to a centralized processing unit; in the case of a headset, an EM apparatus as disclosed herein may be used to enhance an actor's experience at a theme park, or help report the proximity of an object to the actor when engaged in an interactive session via a heads-up display, for example; or, in the case eyeglasses, an EM apparatus as disclosed herein may be used to enhance the peripheral vision of an actor, alert the actor of objects close by that may pose a collision threat, interpret hand gestures, or interpret gestures to adjust device settings such as light filtering lenses for example. While only a few example advantages have been expanded upon herein above, it will be appreciated that an exhaustive listing of potential advantages is not necessary for one skilled in the art to appreciate the potential uses and advantages of a MWRB/MWRBGR system as disclosed herein.

While an invention has been described herein with reference to example embodiments, it will be understood by those skilled in the art that various changes may be made and equivalents may be substituted for elements thereof without departing from the scope of the claims. Many modifications may be made to adapt a particular situation or material to the teachings of the invention without departing from the essential scope thereof. Therefore, it is intended that the invention not be limited to the particular embodiment or embodiments disclosed herein as the best or only mode contemplated for carrying out this invention, but that the invention will include all embodiments falling within the scope of the appended claims. In the drawings and the description, there have been disclosed example embodiments and, although specific terms and/or dimensions may have been employed, they are unless otherwise stated used in a generic, exemplary and/or descriptive sense only and not for purposes of limitation, the scope of the claims therefore not being so limited. When an element is referred to as being "on" another element, it can be directly on the other element, or intervening elements may also be present. In contrast, when an element is referred to as being "directly on" another element, there are no intervening elements present. The use of the terms first, second, etc. do not denote any order or importance, but rather the terms first, second, etc. are used to distinguish one element from another. The use of the terms a, an, etc. do not denote a limitation of quantity, but rather denote the presence of at least one of the referenced item. The term "comprising" as used herein does not exclude the possible inclusion of one or more additional features. And, any background information provided herein is provided to reveal information believed by the applicant to be of possible relevance to the invention disclosed herein. No admission is necessarily intended, nor should be construed, that any of such background information constitutes prior art against an embodiment of the invention disclosed herein.

In view of all of the foregoing, it will be appreciated that various aspects of an embodiment are disclosed, which are in accordance with at least the following.

Aspect 1: A wearable electromagnetic, EM, apparatus, comprising: at least one antenna operable in a millimeter-wave-radar-based, MWRB, application; at least one computer processor disposed in signal communication with the at least one antenna; an attachment system configured and adapted to attach to an actor; the at least one antenna and the at least one computer processor disposed in a supported relationship with the attachment system, such that the attachment system with the supported at least one antenna and the at least one computer processor at least partially forms a wearable apparatus that is wearable by the actor.

Aspect 2: The EM apparatus of Aspect 1, wherein: the at least one antenna is at least one dielectric resonator antenna, DRA.

Aspect 3: The EM apparatus of any of Aspects 1 to 2, wherein: the at least one DRA comprises an array of corresponding ones of the at least one DRA.

Aspect 4: The EM apparatus of any of Aspects 1 to 3, wherein: the actor is a particular mammal, or more particularly a particular human.

Aspect 5: The EM apparatus of any of Aspects 1 to 4, wherein: the at least one antenna and the at least one computer processor at least partially form a millimeter-wave-radar-based-gesture-recognition, MWRBGR, system; the at least one antenna configured and adapted as a monostatic antenna to transmit an EM radiation field and to receive EM radiation reflections from the EM radiation field, the EM radiation reflections based at least partially on a recognized gesture of the actor; the at least one computer processor being responsive to executable instructions which when executed by the at least one computer processor facilitates a particular operation based at least partially on the recognized gesture of the actor.

Aspect 6: The EM apparatus of any of Aspects 1 to 4, wherein: the at least one antenna comprises a plurality of antennas configured and adapted as a bistatic antenna comprising at least one first set of transmitter antennas and at least one second set of receiver antennas; the at least one antenna and the at least one computer processor at least partially form a millimeter-wave-radar-based-gesture-recognition, MWRBGR, system; the at least one first set of transmitter antennas configured and adapted to transmit an EM radiation field; the at least one second set of receiver antennas configured and adapted to receive EM radiation reflections from the EM radiation field, the EM radiation reflections based at least partially on a recognized gesture of the actor; the at least one computer processor being responsive to executable instructions which when executed by the at least one computer processor facilitates a particular operation based at least partially on the recognized gesture of the actor.

Aspect 7: The EM apparatus of Aspect 5, wherein: the monostatic antenna being configured and adapted to receive EM radiation reflections has an effective EM aperture so dimensioned and configured as to enable resolution via the at least one computer processor of the recognized gesture at a distance up to 30 cm from the EM apparatus.

Aspect 8: The EM apparatus of Aspect 6, wherein: the at least one second set of receiver antennas has an effective EM aperture so dimensioned and configured as to enable resolution via the at least one computer processor of the recognized gesture at a distance up to 30 cm from the EM apparatus.

Aspect 9: The EM apparatus of any of Aspects 1 to 8, wherein: the at least one antenna is operable in a frequency range of: equal to or greater than 10 GHz and equal to or less than 400 GHz; or, equal to or greater than 30 GHz and equal to or less than 300 GHz; or, equal to or greater than 50 GHz and equal to or less than 100 GHz; or, equal to or greater than 54 GHz and equal to or less than 66 GHz.

Aspect 10: The EM apparatus of any of Aspects 1 to 9, wherein: the wearable apparatus forms at least part of: a wrist apparatus; a bracelet; a wrist watch; a neck apparatus; a necklace; a neck apparel; a clothing apparatus; a brooch; a head apparatus; a headset; a helmet; a face apparatus; an eyeglass; or, a pair of eyeglasses.

Aspect 11: The EM apparatus of Aspect 8, wherein: the EM apparatus is in signal communication with and forms at least part of an extended reality system.

Aspect 12: The EM apparatus of any of Aspects 10 to 11, wherein: the EM device forms at least part of the wrist apparatus; and the at least one antenna is disposed: on a wristband of the wrist apparatus proximate but not integral with a display portion of the wrist apparatus.

Aspect 13: The EM apparatus of any of Aspects 10 to 11, wherein: the EM device forms at least part of: the neck apparatus; the necklace; the neck apparel; the clothing apparatus; or, the brooch; and the at least one antenna is disposed: proximate a surface of the neck apparatus, the necklace, the neck apparel, the clothing apparatus, or the brooch, that faces substantially toward the actor.

Aspect 14: The EM apparatus of any of Aspects 10 to 11, wherein: the EM device forms at least part of: the head apparatus; the headset; or, the helmet; and the at least one antenna is disposed: proximate a surface of the head apparatus, the headset, or the helmet, that faces substantially away from the actor.

Aspect 15: The EM apparatus of any of Aspects 10 to 11, wherein: the EM device forms at least part of: the face apparatus; the eyeglass; or, the pair of eyeglasses; and the at least one antenna is disposed: proximate a surface of the face apparatus, the eyeglass, or the pair of eyeglasses, that faces substantially away from the actor.

Aspect 16: The EM apparatus of Aspect 15, wherein: the at least one antenna is disposed: proximate but not integral with a lens portion of the eye glass or the pair of eyeglasses.

Aspect 17: The EM apparatus of any of Aspects 5 to 16, wherein: the particular operation based at least partially on the recognized gesture of the actor comprises: dialing a telephone number using a telephone configured and adapted to be in signal communication with the EM apparatus; accepting an incoming telephone call using a telephone configured and adapted to be in signal communication with the EM apparatus; raising or lowering the speaker volume of a telephone configured and adapted to be in signal communication with the EM apparatus; taking a photograph using a camera configured and adapted to be in signal communication with the EM apparatus; opening an electronic contact file using an electronic contact list configured and adapted to be in signal communication with the EM apparatus; measuring a blood pressure of the actor and alerting the actor with the measured value in an event where the EM device is worn by the actor and the blood pressure of the actor is equal to or greater than a first particular value, or is equal to or less than a second particular value; measuring a bone density of the actor and alerting the actor with the measured value in an event where the EM device is worn by the actor and the bone density of the actor is equal to or less than a particular value; measuring a heart rate of the actor and alerting the actor with the measured value in an event where the EM device is worn by the actor and the heart rate of the actor is equal to or greater than a first particular value, or is equal to or less than a second particular value; or, interpreting the recognized gesture as a rapid movement suggestive of a fall and sending an alert communication to a particular recipient other than the actor in an event where the EM device is worn by the actor.

Aspect 18: An electromagnetic, EM, apparatus, comprising: a millimeter-wave-radar-based-gesture-recognition, MWRBGR, system, comprising: at least one antenna operable in a millimeter-wave-radar-based, MWRB, application; at least one computer processor disposed in signal communication with the at least one antenna; the at least one antenna configured and adapted to transmit an EM radiation field and to receive EM radiation reflections from the EM radiation field, the EM radiation reflections based at least partially on a recognized gesture of an actor; the at least one computer processor being responsive to executable instructions which when executed by the at least one computer processor facilitates a particular operation based at least partially on the recognized gesture of the actor.

Aspect 19: The EM apparatus of Aspect 18, wherein: the at least one antenna is at least one dielectric resonator antenna, DRA.

Aspect 20: The EM apparatus of any of Aspects 18 to 19, wherein: the at least one DRA comprises an array of corresponding ones of the at least one DRA.

Aspect 21: The EM apparatus of any of Aspects 18 to 20, wherein: the actor is a particular mammal, or more particularly a particular human.

Aspect 22: The EM apparatus of any of Aspects 18 to 21, wherein: the at least one antenna comprises a plurality of antennas comprising at least one first set of transmitter antennas and at least one second set of receiver antennas.

Aspect 23: The EM apparatus of Aspect 22, wherein: the at least one second set of receiver antennas has an effective EM aperture so dimensioned and configured as to enable resolution of the recognized gesture at a distance up to 30 cm from the EM apparatus.

Aspect 24: The EM apparatus of any of Aspects 18 to 23, wherein: the at least one antenna is operable in a frequency range of: equal to or greater than 10 GHz and equal to or less than 400 GHz; or, equal to or greater than 30 GHz and equal to or less than 300 GHz; or, equal to or greater than 50 GHz and equal to or less than 100 GHz; or, equal to or greater than 54 GHz and equal to or less than 66 GHz.

Aspect 25: The EM apparatus of any of Aspects 22 to 24, wherein: the EM apparatus forms at least part of: a mobile cell phone; a handheld communication device; a mobile computing device; or, a network extender device.

Aspect 26: The EM apparatus of any of Aspects 22 to 25, wherein: the EM apparatus is in signal communication with and forms at least part of an extended reality system.

Aspect 27: The EM apparatus of any of Aspects 25 to 26, wherein: the EM device forms at least part of the mobile cell phone; and the at least one antenna is disposed: proximate a rear side of the phone; or, proximate an outer edge of the phone.

Aspect 28: The EM apparatus of any of Aspects 25 to 26, wherein: the EM device forms at least part of the mobile computing device operable by a user; and the at least one antenna is disposed: proximate a surface of the mobile computing device that faces substantially away from the user; or, proximate a surface of the mobile computing device that faces substantially toward the user.

Aspect 29: A wearable electromagnetic, EM, apparatus, comprising: at least one antenna operable in a millimeter-wave frequency, the at least one antenna comprising a dielectric resonator antenna, DRA, array; at least one computer processor disposed in signal communication with the at least one antenna; an attachment system configured and adapted to attach to an actor; the at least one antenna and the at least one computer processor disposed in a supported relationship with the attachment system, such that the attachment system with the supported at least one antenna and the at least one computer processor at least partially forms a wearable apparatus that is wearable by the actor.

Aspect 30: The EM apparatus of Aspect 29, wherein: the at least one antenna is at least one dielectric resonator antenna, DRA.

Aspect 31: The EM apparatus of any of Aspects 29 to 30, wherein: the at least one DRA comprises an array of corresponding ones of the at least one DRA.

Aspect 32: The EM apparatus of any of Aspects 29 to 31, wherein: the actor is a particular mammal, or more particularly a particular human.

Aspect 33: The EM apparatus of any of Aspects 29 to 32, wherein: the at least one antenna comprises a plurality of antennas comprising at least one first set of transmitter antennas and at least one second set of receiver antennas.

Aspect 34: The EM apparatus of Aspect 33, wherein: the at least one second set of receiver antennas has an effective EM aperture so dimensioned and configured as to enable resolution of the recognized gesture at a distance up to 30 cm from the EM apparatus.

Aspect 35: The EM apparatus of any of Aspects 29 to 34, wherein: the at least one antenna is operable in a frequency range of: equal to or greater than 10 GHz and equal to or less than 400 GHz; or, equal to or greater than 30 GHz and equal to or less than 300 GHz; or, equal to or greater than 50 GHz and equal to or less than 100 GHz; or, equal to or greater than 54 GHz and equal to or less than 66 GHz.

Aspect 36: The EM apparatus of any of the foregoing Aspects, wherein: the at least one antenna is a DRA comprising: an electrically conductive ground structure; a plurality of volumes of dielectric materials disposed on the ground structure comprising N volumes, N being an integer equal to or greater than 3, disposed to form successive and sequential layered volumes V(i), i being an integer from 1 to N, wherein volume V(1) forms an innermost volume, wherein a successive volume V(i+1) forms a layered shell disposed over and at least partially embedding volume V(i), wherein volume V(N) at least partially embeds all volumes V(1) to V(N−1); and a signal feed disposed and structured to be electromagnetically coupled to one or more of the plurality of volumes of dielectric materials.

Aspect 37: The EM apparatus of Aspect 36, further comprising: a power supply disposed in signal communication with the at least one computer processor; at least one transmission unit disposed in signal communication with the at least one computer processor; the at least one transmission unit disposed and configured in signal communication with the at least one antenna; at least one reception unit disposed in signal communication with the at least one computer processor; the at least one reception unit disposed and configured in signal communication with the at least one antenna.

Aspect 38: The EM apparatus of Aspect 37, wherein: the at least one transmission unit disposed and configured in signal communication with the at least one antenna is disposed and configured in signal communication with at least one transmit antenna.

Aspect 39: The EM apparatus of any of Aspects 37 to 38, wherein: the at least one reception unit disposed and configured in signal communication with the at least one antenna is disposed and configured in signal communication with at least one receive antenna.

Aspect 40: The EM apparatus of any of Aspects 36 to 39, wherein: volume V(1) comprises air.

Aspect 41: The EM apparatus of any of Aspects 36 to 39, wherein: volume V(2) comprises a dielectric material other than air.

Aspect 42: The EM apparatus of any of Aspects 36 to 40, wherein: volume V(N) comprises air.

Aspect 43: The EM apparatus of any of Aspects 36 to 40, wherein: the DRA is a first dielectric portion, 1DP, having a proximal end and a distal end, and the EM apparatus further comprises a second dielectric portion, 2DP, having a proximal end and a distal end, the proximal end of the 2DP being disposed proximate the distal end of the 1DP to form the dielectric structure, the 2DP comprising a dielectric material other than air.

Aspect 44: The EM apparatus of Aspect 43, wherein: the dielectric material of the 1DP has an average dielectric constant that is greater than the average dielectric constant of the dielectric material of the 2DP.

Aspect 45: The EM apparatus of any of Aspects 36 to 44, wherein: the DRA comprises a plurality of respective ones of the DRA to form a DRA array.

The invention claimed is:

1. An electromagnetic, EM, apparatus that is wearable, comprising:
at least one antenna operable in a millimeter-wave-radar-based, MWRB, application;
at least one computer processor disposed in signal communication with the at least one antenna;
an attachment system configured and adapted to attach to a particular actor;
the at least one antenna and the at least one computer processor disposed in a supported relationship with the attachment system, such that the attachment system with the supported at least one antenna and the at least one computer processor at least partially forms the wearable apparatus that is wearable by the actor;
wherein the at least one antenna is at least one dielectric resonator antenna, DRA;
wherein the DRA is a first dielectric portion, 1DP, having a proximal end and a distal end, wherein the proximal end of the 1DP is disposed on an electrically conductive ground structure;
wherein the EM apparatus further comprises a second dielectric portion, 2DP, having a proximal end and a distal end, the proximal end of the 2DP being disposed in direct contact with the distal end of the 1DP to form a dielectric structure, the 2DP comprising a dielectric material other than air; and
wherein the dielectric material of the 1DP has an average dielectric constant that is greater than the average dielectric constant of the dielectric material of the 2DP.

2. The EM apparatus of claim 1, wherein:
the at least one DRA comprises an array of corresponding ones of the at least one DRA.

3. The EM apparatus of claim 1, wherein:
the actor is a particular mammal, or more particularly a particular human.

4. The EM apparatus of claim 1, wherein:
the at least one antenna and the at least one computer processor at least partially form a millimeter-wave-radar-based-gesture-recognition, MWRBGR, system;
the at least one antenna configured and adapted as a monostatic antenna to transmit an EM radiation field and to receive EM radiation reflections from the EM radiation field, the EM radiation reflections based at least partially on a recognized gesture of the actor;
the at least one computer processor being responsive to executable instructions which when executed by the at least one computer processor facilitates a particular operation based at least partially on the recognized gesture of the actor.

5. The EM apparatus of claim 1, wherein:
the at least one antenna comprises a plurality of antennas configured and adapted as a bistatic antenna comprising at least one first set of transmitter antennas and at least one second set of receiver antennas;
the at least one antenna and the at least one computer processor at least partially form a millimeter-wave-radar-based-gesture-recognition, MWRBGR, system;
the at least one first set of transmitter antennas configured and adapted to transmit an EM radiation field;
the at least one second set of receiver antennas configured and adapted to receive EM radiation reflections from the EM radiation field, the EM radiation reflections based at least partially on a recognized gesture of the actor;
the at least one computer processor being responsive to executable instructions which when executed by the at least one computer processor facilitates a particular operation based at least partially on the recognized gesture of the actor.

6. The EM apparatus of claim 4, wherein:
the monostatic antenna being configured and adapted to receive EM radiation reflections has an effective EM aperture so dimensioned and configured as to enable resolution via the at least one computer processor of the recognized gesture at a distance up to 30 cm from the EM apparatus.

7. The EM apparatus of claim 5, wherein:
the at least one second set of receiver antennas has an effective EM aperture so dimensioned and configured as to enable resolution via the at least one computer processor of the recognized gesture at a distance up to 30 cm from the EM apparatus.

8. The EM apparatus of claim 1, wherein:
the at least one antenna is operable in a frequency range of: equal to or greater than 10 GHz and equal to or less than 400 GHz; or, equal to or greater than 30 GHz and equal to or less than 300 GHz; or, equal to or greater than 50 GHz and equal to or less than 100 GHz; or, equal to or greater than 54 GHz and equal to or less than 66 GHz.

9. The EM apparatus of claim 1, wherein:
the EM apparatus forms at least part of: a wrist apparatus; a bracelet; a wrist watch; a neck apparatus; a necklace; a neck apparel; a clothing apparatus; a brooch; a head apparatus; a headset; a helmet; a face apparatus; an eyeglass; or, a pair of eyeglasses.

10. The EM apparatus of claim 7, wherein:
the EM apparatus is in signal communication with and forms at least part of an extended reality system.

11. The EM apparatus of claim 9, wherein:
the EM device forms at least part of the wrist apparatus; and
the at least one antenna is disposed: on a wristband of the wrist apparatus proximate but not integral with a display portion of the wrist apparatus.

12. The EM apparatus of claim 9, wherein:
the EM device forms at least part of: the neck apparatus; the necklace; the neck apparel; the clothing apparatus; or, the brooch; and the at least one antenna is disposed: proximate a surface of the neck apparatus, the necklace, the neck apparel, the clothing apparatus, or the brooch, that faces toward the actor.

13. The EM apparatus of claim 9, wherein:
the EM device forms at least part of: the head apparatus; the headset; or, the helmet; and
the at least one antenna is disposed: proximate a surface of the head apparatus, the headset, or the helmet, that faces away from the actor.

14. The EM apparatus of claim 9, wherein:
the EM device forms at least part of: the face apparatus; the eyeglass; or, the pair of eyeglasses; and
the at least one antenna is disposed: proximate a surface of the face apparatus, the eyeglass, or the pair of eyeglasses, that faces away from the actor.

15. The EM apparatus of claim 14, wherein:
the at least one antenna is disposed: proximate but not integral with a lens portion of the eye glass or the pair of eyeglasses.

16. The EM apparatus of claim 4, wherein:
the particular operation based at least partially on the recognized gesture of the actor comprises: dialing a telephone number using a telephone configured and adapted to be in signal communication with the EM apparatus; accepting an incoming telephone call using a telephone configured and adapted to be in signal communication with the EM apparatus; raising or lowering the speaker volume of a telephone configured and adapted to be in signal communication with the EM apparatus; taking a photograph using a camera configured and adapted to be in signal communication with the EM apparatus; opening an electronic contact file using an electronic contact list configured and adapted to be in signal communication with the EM apparatus; measuring a blood pressure of the actor and alerting the actor with the measured value in an event where the EM device is worn by the actor and the blood pressure of the actor is equal to or greater than a first particular value, or is equal to or less than a second particular value; measuring a bone density of the actor and alerting the actor with the measured value in an event where the EM device is worn by the actor and the bone density of the actor is equal to or less than a particular value; measuring a heart rate of the actor and alerting the actor with the measured value in an event where the EM device is worn by the actor and the heart rate of the actor is equal to or greater than a first particular value, or is equal to or less than a second particular value; or, interpreting the recognized gesture as a rapid movement suggestive of a fall and sending an alert communication to a particular recipient other than the actor in an event where the EM device is worn by the actor.

17. An electromagnetic, EM, apparatus, comprising:
a millimeter-wave-radar-based-gesture-recognition, MWRBGR, system, comprising:
at least one antenna operable in a millimeter-wave-radar-based, MWRB, application;
at least one computer processor disposed in signal communication with the at least one antenna;
the at least one antenna configured and adapted to transmit an EM radiation field and to receive EM radiation reflections from the EM radiation field, the EM radiation reflections based at least partially on a recognized gesture of a particular actor;
the at least one computer processor being responsive to executable instructions which when executed by the at least one computer processor facilitates a particular operation based at least partially on the recognized gesture of the actor;
wherein the at least one antenna is at least one dielectric resonator antenna, DRA;
wherein the DRA is a first dielectric portion, 1DP, having a proximal end and a distal end, wherein the proximal end of the 1DP is disposed on an electrically conductive ground structure;
wherein the EM apparatus further comprises a second dielectric portion, 2DP, having a proximal end and a distal end, the proximal end of the 2DP being disposed in direct contact with the distal end of the 1DP to form a dielectric structure, the 2DP comprising a dielectric material other than air; and
wherein the dielectric material of the 1DP has an average dielectric constant that is greater than the average dielectric constant of the dielectric material of the 2DP.

18. The EM apparatus of claim 17, wherein:
the at least one antenna is at least one dielectric resonator antenna, DRA.

19. The EM apparatus of claim 17, wherein:
the at least one DRA comprises an array of corresponding ones of the at least one DRA.

20. The EM apparatus of claim 17, wherein:
the actor is a particular mammal, or more particularly a particular human.

21. The EM apparatus of claim 17, wherein:
the at least one antenna comprises a plurality of antennas comprising at least one first set of transmitter antennas and at least one second set of receiver antennas.

22. The EM apparatus of claim 21, wherein:
the at least one second set of receiver antennas has an effective EM aperture so dimensioned and configured as to enable resolution of the recognized gesture at a distance up to 30 cm from the EM apparatus.

23. The EM apparatus of claim 17, wherein:
the at least one antenna is operable in a frequency range of: equal to or greater than 10 GHz and equal to or less than 400 GHz; or, equal to or greater than 30 GHz and equal to or less than 300 GHz; or, equal to or greater than 50 GHz and equal to or less than 100 GHz; or, equal to or greater than 54 GHz and equal to or less than 66 GHz.

24. The EM apparatus of claim 21, wherein:
the EM apparatus forms at least part of: a mobile cell phone; a handheld communication device; a mobile computing device; or, a network extender device.

25. The EM apparatus of claim 21, wherein:
the EM apparatus is in signal communication with and forms at least part of an extended reality system.

26. The EM apparatus of claim 24, wherein:
the EM apparatus forms at least part of the mobile cell phone; and
the at least one antenna is disposed: proximate a rear side of the phone; or, proximate an outer edge of the phone.

27. The EM apparatus of claim 24, wherein:
the EM apparatus forms at least part of the mobile computing device operable by a user; and
the at least one antenna is disposed: proximate a surface of the mobile computing device that faces away from the user; or, proximate a surface of the mobile computing device that faces toward the user.

28. An electromagnetic, EM, apparatus that is wearable, comprising:

at least one antenna operable in a millimeter-wave frequency, the at least one antenna comprising a dielectric resonator antenna, DRA, array;

at least one computer processor disposed in signal communication with the at least one antenna;

an attachment system configured and adapted to attach to a particular actor;

the at least one antenna and the at least one computer processor disposed in a supported relationship with the attachment system, such that the attachment system with the supported at least one antenna and the at least one computer processor at least partially forms the wearable apparatus that is wearable by the actor;

wherein the at least one antenna is at least one dielectric resonator antenna, DRA;

wherein the DRA is a first dielectric portion, 1DP, having a proximal end and a distal end, wherein the proximal end of the 1DP is disposed on an electrically conductive ground structure;

wherein the EM apparatus further comprises a second dielectric portion, 2DP, having a proximal end and a distal end, the proximal end of the 2DP being disposed in direct contact with the distal end of the 1DP to form a dielectric structure, the 2DP comprising a dielectric material other than air; and wherein the dielectric material of the 1DP has an average dielectric constant that is greater than the average dielectric constant of the dielectric material of the 2DP.

29. The EM apparatus of claim 28, wherein:
the at least one DRA comprises an array of corresponding ones of the at least one DRA.

30. The EM apparatus of claim 28, wherein:
the actor is a particular mammal, or more particularly a particular human.

31. The EM apparatus of claim 28, wherein:
the at least one antenna comprises a plurality of antennas comprising at least one first set of transmitter antennas and at least one second set of receiver antennas.

32. The EM apparatus of claim 31, wherein:
the at least one second set of receiver antennas has an effective EM aperture so dimensioned and configured as to enable resolution of the recognized gesture at a distance up to 30 cm from the EM apparatus.

33. The EM apparatus of claim 28, wherein:
the at least one antenna is operable in a frequency range of: equal to or greater than 10 GHz and equal to or less than 400 GHz; or, equal to or greater than 30 GHz and equal to or less than 300 GHz; or, equal to or greater than 50 GHz and equal to or less than 100 GHz; or, equal to or greater than 54 GHz and equal to or less than 66 GHz.

34. The EM apparatus of claim 1, wherein:
the at least one DRA comprises: a plurality of volumes of dielectric materials disposed on the ground structure comprising N volumes, N being an integer equal to or greater than 3, disposed to form successive and sequential layered volumes V(i), i being an integer from 1 to N, wherein volume V(1) forms an innermost volume, wherein a successive volume V(i+1) forms a layered shell disposed over and at least partially embedding volume V(i), wherein volume V(N) at least partially embeds all volumes V(1) to V(N−1); and a signal feed disposed and structured to be electromagnetically coupled to one or more of the plurality of volumes of dielectric materials.

35. The EM apparatus of claim 34, further comprising:
a power supply disposed in signal communication with the at least one computer processor;

at least one transmission unit disposed in signal communication with the at least one computer processor;

the at least one transmission unit disposed and configured in signal communication with the at least one antenna;

at least one reception unit disposed in signal communication with the at least one computer processor;

the at least one reception unit disposed and configured in signal communication with the at least one antenna.

36. The EM apparatus of claim 35, wherein:
the at least one transmission unit disposed and configured in signal communication with the at least one antenna is disposed and configured in signal communication with at least one transmit antenna.

37. The EM apparatus of claim 35, wherein:
the at least one reception unit disposed and configured in signal communication with the at least one antenna is disposed and configured in signal communication with at least one receive antenna.

38. The EM apparatus of claim 34, wherein:
volume V(1) comprises air.

39. The EM apparatus of claim 34, wherein:
volume V(2) comprises a dielectric material other than air.

40. The EM apparatus of claim 34, wherein:
volume V(N) comprises air.

41. The EM apparatus of claim 34, wherein:
the at least one DRA comprises a plurality of respective ones of the at least one DRA to form a DRA array.

* * * * *